(12) United States Patent
Shuber

(10) Patent No.: US 7,981,607 B2
(45) Date of Patent: Jul. 19, 2011

(54) METHOD FOR DETECTING RECOMBINANT EVENT

(75) Inventor: Anthony P. Shuber, Mendon, MA (US)

(73) Assignee: Esoterix Genetic Laboratories LLC, Burlington, NC (US)

( * ) Notice: Subject to any disclaimer, the term of this patent is extended or adjusted under 35 U.S.C. 154(b) by 0 days.

(21) Appl. No.: 11/661,528

(22) PCT Filed: Aug. 29, 2005

(86) PCT No.: PCT/US2005/030942

§ 371 (c)(1),
(2), (4) Date: Feb. 9, 2009

(87) PCT Pub. No.: WO2006/026654

PCT Pub. Date: Mar. 9, 2006

(65) Prior Publication Data

US 2009/0170077 A1    Jul. 2, 2009

Related U.S. Application Data

(60) Provisional application No. 60/604,870, filed on Aug. 27, 2004.

(51) Int. Cl.
C12Q 1/68 (2006.01)
C12P 19/34 (2006.01)

(52) U.S. Cl. .......................................... 435/6; 435/91.2

(58) Field of Classification Search .................. None
See application file for complete search history.

(56) References Cited

U.S. PATENT DOCUMENTS

| | | |
|---|---|---|
| 4,072,574 A | 2/1978 | Loeb et al. |
| 4,101,279 A | 7/1978 | Aslam |
| 4,309,782 A | 1/1982 | Paulin |
| 4,333,734 A | 6/1982 | Fleisher |
| 4,445,235 A | 5/1984 | Slover et al. |
| 4,535,058 A | 8/1985 | Weinberg et al. |
| 4,705,050 A | 11/1987 | Markham |
| 4,786,718 A | 11/1988 | Weinberg et al. |
| 4,857,300 A | 8/1989 | Maksem |
| 4,863,849 A | 9/1989 | Melamede |
| 4,871,838 A | 10/1989 | Bos et al. |
| 4,968,602 A | 11/1990 | Dattagupta |
| 4,968,603 A | 11/1990 | Slamon et al. |
| 4,988,617 A | 1/1991 | Landegren et al. |
| 5,075,217 A | 12/1991 | Weber |
| 5,087,617 A | 2/1992 | Smith |
| 5,126,239 A | 6/1992 | Livak et al. |
| 5,137,806 A | 8/1992 | LeMaistre et al. |
| 5,141,849 A | 8/1992 | Chou |
| 5,149,506 A | 9/1992 | Skiba et al. |
| 5,185,244 A | 2/1993 | Wallace |
| 5,196,167 A | 3/1993 | Guadagno et al. |
| 5,202,231 A | 4/1993 | Drmanac et al. |
| 5,248,671 A | 9/1993 | Smith |
| 5,272,057 A | 12/1993 | Smulson et al. |
| 5,296,349 A | 3/1994 | Wallace |
| 5,302,509 A | 4/1994 | Cheeseman |
| 5,330,892 A | 7/1994 | Vogelstein et al. |
| 5,331,973 A | 7/1994 | Fiedler et al. |
| 5,348,855 A | 9/1994 | Dattagupta et al. |
| 5,352,775 A | 10/1994 | Albertsen et al. |
| 5,362,623 A | 11/1994 | Vogelstein et al. |
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar |
| 5,382,510 A | 1/1995 | Levine et al. |
| 5,409,586 A | 4/1995 | Kamahori et al. |
| 5,455,166 A | 10/1995 | Walker |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,489,508 A | 2/1996 | West et al. |
| 5,492,808 A | 2/1996 | de la Chapelle et al. |
| 5,496,470 A | 3/1996 | Lenhart |
| 5,496,699 A | 3/1996 | Sorenson |
| 5,508,164 A | 4/1996 | Kausch et al. |
| 5,512,441 A | 4/1996 | Ronai |
| 5,514,547 A | 5/1996 | Balazs et al. |
| 5,527,676 A | 6/1996 | Vogelstein et al. |
| 5,532,108 A | 7/1996 | Vogelstein |
| 5,545,527 A | 8/1996 | Stevens et al. |
| 5,552,283 A | 9/1996 | Diamandis et al. |

(Continued)

FOREIGN PATENT DOCUMENTS

AU    A-11325/95    4/1996

(Continued)

OTHER PUBLICATIONS

Aaltonen et al (1994) "Replication Errors in Benign and Malignant Tumors from Hereditary Nonpolyposis Colorectal Cancer Patients" Cancer Research 54:1645-1648.

(Continued)

Primary Examiner — James Martinell
(74) Attorney, Agent, or Firm — Kilpatrick Townsend & Stockton LLP

(57) ABSTRACT

Methods relating to isolating and amplifying chimeric nucleic acid molecules are provided. The methods of the invention are useful for detecting chromosome translocation events associated with diseases or conditions, such as cancer.

9 Claims, 2 Drawing Sheets

U.S. PATENT DOCUMENTS

| | | | |
|---|---|---|---|
| 5,561,041 A | 10/1996 | Sidransky | |
| 5,569,584 A | 10/1996 | Augenlicht | |
| 5,571,676 A | 11/1996 | Shuber | |
| 5,578,458 A | 11/1996 | Caskey et al. | |
| 5,589,330 A | 12/1996 | Shuber | |
| 5,589,335 A | 12/1996 | Kearney et al. | |
| 5,604,099 A | 2/1997 | Erlich et al. | |
| 5,610,287 A | 3/1997 | Nikiforov et al. | |
| 5,616,463 A | 4/1997 | Fornace, Jr. et al. | |
| 5,627,032 A | 5/1997 | Ulanovsky | |
| 5,633,134 A | 5/1997 | Shuber | |
| 5,635,347 A | 6/1997 | Link et al. | |
| 5,635,352 A | 6/1997 | Urdea et al. | |
| 5,645,995 A | 7/1997 | Kieback | |
| 5,648,212 A | 7/1997 | Albertsen et al. | |
| 5,650,277 A | 7/1997 | Navot et al. | |
| 5,650,281 A | 7/1997 | Vogelstein | |
| 5,670,325 A | 9/1997 | Lapidus et al. | |
| 5,683,877 A | 11/1997 | Lu-Chang et al. | |
| 5,687,716 A | 11/1997 | Kaufmann et al. | |
| 5,709,998 A | 1/1998 | Kinzler et al. | |
| 5,710,028 A | 1/1998 | Eyal et al. | |
| 5,726,019 A | 3/1998 | Sidransky | |
| 5,741,650 A | 4/1998 | Lapidus et al. | |
| 5,753,439 A | 5/1998 | Smith et al. | |
| 5,759,777 A | 6/1998 | Kearney et al. | |
| 5,798,266 A | 8/1998 | Quay et al. | |
| 5,830,665 A | 11/1998 | Shuber et al. | |
| 5,834,181 A | 11/1998 | Shuber | |
| 5,834,193 A | 11/1998 | Kozlowski et al. | |
| 5,846,710 A | 12/1998 | Bajaj | |
| 5,856,092 A | 1/1999 | Dale et al. | |
| 5,866,323 A | 2/1999 | Markowitz et al. | |
| 5,885,775 A | 3/1999 | Haff et al. | |
| 5,888,778 A | 3/1999 | Shuber | |
| 5,888,819 A | 3/1999 | Goelet et al. | |
| 5,910,407 A | 6/1999 | Vogelstein et al. | |
| 5,928,870 A | 7/1999 | Lapidus et al. | |
| 5,945,284 A | 8/1999 | Livak et al. | |
| 5,952,178 A | 9/1999 | Lapidus et al. | |
| 5,958,684 A | 9/1999 | Van Leeuwen et al. | |
| 5,976,798 A | 11/1999 | Parker et al. | |
| 5,976,842 A | 11/1999 | Wurst | |
| 5,981,180 A | 11/1999 | Chandler et al. | |
| 6,013,431 A | 1/2000 | Soderlund et al. | |
| 6,017,704 A | 1/2000 | Herman et al. | |
| 6,020,124 A | 2/2000 | Sorenson | |
| 6,020,137 A | 2/2000 | Lapidus et al. | |
| 6,084,091 A | 7/2000 | Muller et al. | |
| 6,100,029 A | 8/2000 | Lapidus et al. | |
| 6,100,040 A | 8/2000 | Ramberg | |
| 6,107,032 A | 8/2000 | Kilger et al. | |
| 6,107,061 A | 8/2000 | Johnson | |
| 6,110,678 A | 8/2000 | Weisburg et al. | |
| 6,114,114 A | 9/2000 | Seilhamer et al. | |
| 6,130,049 A | 10/2000 | Paul et al. | |
| 6,143,529 A | 11/2000 | Lapidus et al. | |
| 6,146,828 A | 11/2000 | Lapidus et al. | |
| 6,150,117 A | 11/2000 | Zetter et al. | |
| 6,153,379 A | 11/2000 | Caskey et al. | |
| 6,177,251 B1 | 1/2001 | Vogelstein et al. | |
| 6,180,408 B1 | 1/2001 | Kwok et al. | |
| 6,203,993 B1 | 3/2001 | Shuber et al. | |
| 6,214,558 B1 | 4/2001 | Shuber et al. | |
| 6,221,592 B1 | 4/2001 | Schwartz et al. | |
| 6,225,092 B1 | 5/2001 | Kilger et al. | |
| 6,228,596 B1 | 5/2001 | Macina et al. | |
| 6,235,486 B1 | 5/2001 | Young et al. | |
| 6,251,638 B1 | 6/2001 | Umansky et al. | |
| 6,258,540 B1 | 7/2001 | Lo et al. | |
| 6,265,229 B1 | 7/2001 | Fodstad et al. | |
| 6,268,136 B1 | 7/2001 | Shuber et al. | |
| 6,280,947 B1 | 8/2001 | Shuber et al. | |
| 6,300,077 B1 | 10/2001 | Shuber et al. | |
| 6,303,304 B1 | 10/2001 | Shuber et al. | |
| 6,312,893 B1 | 11/2001 | Van Ness et al. | |
| 6,351,857 B2 | 3/2002 | Slaon, III et al. | |
| 6,355,433 B1 | 3/2002 | Xu et al. | |
| 6,361,940 B1 | 3/2002 | Van Ness et al. | |
| 6,406,857 B1 | 6/2002 | Shuber et al. | |
| 6,415,555 B1 | 7/2002 | Montague | |
| 6,428,964 B1 | 8/2002 | Shuber | |
| 6,458,544 B1 | 10/2002 | Miller | |
| 6,475,738 B2 | 11/2002 | Shuber et al. | |
| 6,482,595 B2 | 11/2002 | Shuber et al. | |
| 6,498,012 B2 | 12/2002 | Laken | |
| 6,503,718 B2 | 1/2003 | Shuber et al. | |
| 6,518,026 B2 | 2/2003 | Hartley | |
| 6,534,273 B2 * | 3/2003 | Weisburg et al. | 435/6 |
| 6,551,777 B1 | 4/2003 | Shuber et al. | |
| 6,566,101 B1 | 5/2003 | Shuber et al. | |
| 6,586,177 B1 | 7/2003 | Shuber | |
| 6,605,433 B1 | 8/2003 | Fliss et al. | |
| 6,818,404 B2 | 11/2004 | Shuber | |
| 6,844,155 B2 | 1/2005 | Shuber | |
| 6,919,174 B1 | 7/2005 | Shuber | |
| 7,432,050 B2 | 10/2008 | Markowitz | |
| 7,485,420 B2 | 2/2009 | Markowitz | |
| 2001/0018180 A1 | 8/2001 | Shuber et al. | |
| 2001/0039012 A1 | 11/2001 | Lapidus | |
| 2001/0042264 A1 | 11/2001 | Sloan, III et al. | |
| 2002/0001800 A1 | 1/2002 | Lapidus | |
| 2002/0004201 A1 | 1/2002 | Lapidus et al. | |
| 2002/0009727 A1 | 1/2002 | Schultz et al. | |
| 2002/0012922 A1 | 1/2002 | Hilbush et al. | |
| 2002/0025525 A1 | 2/2002 | Shuber | |
| 2002/0040498 A1 | 4/2002 | Sloan et al. | |
| 2002/0045183 A1 | 4/2002 | Shuber et al. | |
| 2002/0048752 A1 | 4/2002 | Lapidus et al. | |
| 2002/0064787 A1 | 5/2002 | Shuber et al. | |
| 2002/0102604 A1 | 8/2002 | Milne Edwards et al. | |
| 2002/0110810 A1 | 8/2002 | Shuber | |
| 2002/0119469 A1 | 8/2002 | Shuber et al. | |
| 2002/0119472 A1 | 8/2002 | Lapidus et al. | |
| 2002/0123052 A1 | 9/2002 | Laken | |
| 2002/0132251 A1 | 9/2002 | Shuber | |
| 2002/0164631 A1 | 11/2002 | Shuber et al. | |
| 2003/0044780 A1 | 3/2003 | Lapidus et al. | |
| 2003/0049659 A1 | 3/2003 | Lapidus et al. | |
| 2003/0087258 A1 | 5/2003 | Shuber | |
| 2005/0247563 A1 | 11/2005 | Shuber et al. | |
| 2008/0145852 A1 | 6/2008 | Shuber | |

FOREIGN PATENT DOCUMENTS

| | | |
|---|---|---|
| EP | 0 063 879 A2 | 11/1982 |
| EP | 0 185 494 A2 | 6/1986 |
| EP | 0 284 362 A2 | 9/1988 |
| EP | 0 332 435 A2 | 9/1989 |
| EP | 0 337 498 A2 | 10/1989 |
| EP | 0 063 879 B1 | 11/1989 |
| EP | 0 390 323 A2 | 10/1990 |
| EP | 0 390 323 A3 | 10/1990 |
| EP | 0 407 789 A1 | 1/1991 |
| EP | 0 407 789 B1 | 1/1991 |
| EP | 0 408 918 A1 | 1/1991 |
| EP | 0 332 435 B1 | 4/1992 |
| EP | 0 497 527 A1 | 8/1992 |
| EP | 0 408 918 B1 | 11/1993 |
| EP | 0 608 004 A2 | 7/1994 |
| EP | 0 259 031 B1 | 11/1994 |
| EP | 0 664 339 A1 | 7/1995 |
| EP | 1 251 183 A2 | 10/2002 |
| GB | 2 293 238 A | 3/1996 |
| WO | WO-89/11211 | 11/1989 |
| WO | WO-90/09455 | 8/1990 |
| WO | WO-91/02087 | 2/1991 |
| WO | WO-91/13075 | 9/1991 |
| WO | WO-92/13103 | 8/1992 |
| WO | WO-92/15712 | 9/1992 |
| WO | WO-92/16657 | 10/1992 |
| WO | WO-93/06240 | 4/1993 |
| WO | WO-93/18186 | 9/1993 |
| WO | WO-93/20233 | 10/1993 |
| WO | WO-93/20235 | 10/1993 |
| WO | WO-93/25563 | 12/1993 |
| WO | WO-94/00603 | 1/1994 |
| WO | WO-94/01447 | 1/1994 |

| | | |
|---|---|---|
| WO | WO-94/09161 | 4/1994 |
| WO | WO-94/10575 | 5/1994 |
| WO | WO-94/11383 | 5/1994 |
| WO | WO-94/23055 | 10/1994 |
| WO | WO-95/00669 | 1/1995 |
| WO | WO-95/07361 | 3/1995 |
| WO | WO-95/09928 | 4/1995 |
| WO | WO-95/09929 | 4/1995 |
| WO | WO-95/12606 | 5/1995 |
| WO | WO-95/12607 | 5/1995 |
| WO | WO-95/13397 | 5/1995 |
| WO | WO-95/14108 | 5/1995 |
| WO | WO-95/15400 | 6/1995 |
| WO | WO-95/16792 | 6/1995 |
| WO | WO-95/18818 | 7/1995 |
| WO | WO-95/19448 | 7/1995 |
| WO | WO-95/20680 | 8/1995 |
| WO | WO-95/25813 | 9/1995 |
| WO | WO-95/31728 | 11/1995 |
| WO | WO-96/01907 | 1/1996 |
| WO | WO-96/02671 | 2/1996 |
| WO | WO-96/06951 | 3/1996 |
| WO | WO-96/08514 | 3/1996 |
| WO | WO-96/12821 | 5/1996 |
| WO | WO-96/13611 | 5/1996 |
| WO | WO-96/23895 A | 8/1996 |
| WO | WO-96/30545 | 10/1996 |
| WO | WO-97/09449 | 3/1997 |
| WO | WO-97/09600 | 3/1997 |
| WO | WO-97/22719 | 6/1997 |
| WO | WO-97/23651 | 7/1997 |
| WO | WO-97/25442 | 7/1997 |
| WO | WO-97/28450 | 8/1997 |
| WO | WO-98/13522 | 4/1998 |
| WO | WO-98/14616 | 4/1998 |
| WO | WO-98/38338 | 9/1998 |
| WO | WO-98/39474 | 9/1998 |
| WO | WO-98/39478 | 9/1998 |
| WO | WO-98/58081 | 12/1998 |
| WO | WO-98/58084 | 12/1998 |
| WO | WO-99/20798 | 4/1999 |
| WO | WO-99/28507 | 6/1999 |
| WO | WO-99/43851 | 9/1999 |
| WO | WO-99/45147 | 9/1999 |
| WO | WO-99/53316 | 10/1999 |
| WO | WO-99/55912 | 11/1999 |
| WO | WO-99/60160 | 11/1999 |
| WO | WO-99/60161 | 11/1999 |
| WO | WO-99/60162 | 11/1999 |
| WO | WO-99/66077 | 12/1999 |
| WO | WO-00/09751 | 2/2000 |
| WO | WO-00/11215 | 3/2000 |
| WO | WO-00/31298 | 6/2000 |
| WO | WO-00/31303 | 6/2000 |
| WO | WO-00/31305 | 6/2000 |
| WO | WO-00/32820 | 6/2000 |
| WO | WO-00/42223 | 7/2000 |
| WO | WO-00/50640 | 8/2000 |
| WO | WO-00/58514 | 10/2000 |
| WO | WO-00/61808 | 10/2000 |
| WO | WO-00/66005 | 11/2000 |
| WO | WO-00/70096 | 11/2000 |
| WO | WO-01/11083 | 2/2001 |
| WO | WO-01/18252 | 3/2001 |
| WO | WO-01/42502 | 6/2001 |
| WO | WO-01/42503 | 6/2001 |
| WO | WO-01/42781 | 6/2001 |
| WO | WO-01/64950 A2 | 9/2001 |
| WO | WO-02/055740 | 7/2002 |
| WO | WO-02/059379 | 8/2002 |
| WO | WO-02/074995 | 9/2002 |
| WO | WO-02/092858 | 11/2002 |
| WO | WO-02/099126 | 12/2002 |
| WO | WO-03/044217 | 5/2003 |
| WO | WO-03/071252 | 8/2003 |
| WO | WO-03/104427 A | 12/2003 |
| WO | WO-03/071252 A3 | 1/2004 |
| WO | WO-2004/007773 | 1/2004 |
| WO | WO-2004/113574 A | 12/2004 |
| WO | WO-2005/017207 A2 | 2/2005 |
| WO | WO-2005/111244 A3 | 6/2006 |
| WO | WO-2007/044071 A3 | 1/2008 |

OTHER PUBLICATIONS

Aaltonen et al (1998) "Incidence of Hereditary Nonpolyposis Colorectal Cancer and the Feasibility of Molecular Screening for the Disease" The New England Journal of Medicine 338:1481-1487.

Abarzua et al (1984) "Enzymatic techniques for the isolation of random single-base substitutions in vitro at high frequency" Proc. Natl. Acad. Sci., 81:2030-2034.

Agathanggelou et al. (2001) "Methylation associated inactivation of RASSF1A from region 3p21.3 in lung, breast and ovarian tumours," Oncogene 20(12):1509-18.

Agathanggelou et al. (2003) "Epigenetic inactivation of the candidate 3p21.3 suppressor gene BLU in human cancers," Oncogene 22(10):1580-8.

Agathanggelou et al. (2003) "Identification of novel gene expression targets for the Ras association domain family 1 (RASSF1A) tumor suppressor gene in non-small celllung cancer and neuroblastoma," Cancer Res. 63(17):5344-51.

Agathanggelou et al. (2005) "Role of the Ras-association domain family 1 tumor suppressor gene in human cancers," Cancer Res. 65(9):3497-508. Erratum in: Cancer Res. 65(12):5480.

Ahlquist et al (2000) "Colorectal Cancer Screening by Detection of Altered Human DNA in Stool: Feasibility of a Multitarget Assay Panel" Gastroenterology, 119:1219-1227.

Akino et al. (2005) "The Ras Effector RASSF2 is a Novel Tumor-Suppressor Gene in Human Colorectal Cancer." Gastroenterology, 129:156-169.

Alonzo et al. (2007) "Statistical methods for evaluating DNA methylation as a marker for early detection or prognosis," Disease Markers, 23:113-120.

Ausubel et al. (1995) Short Protocols in Molecular Biology, 3d ed., pp. 2-3-2-12, 3-30-3-33.

Azhikina et al (1996) "Factors affecting the priming efficiency of short contiguous oligonucleotide strings in the primer walking strategy of DNA sequencing" DNA Sequence—The Journal of Sequencing and Mapping, 6:211-216.

Beck (1987) "Colorimetric-detected DNA sequencing" Anal. Biochem., 164(2):514-520. Abstract only.

Behn et al. (1998) "Frequent detection of ras and p53 mutations in brush cytology samples from lung cancer patients by a restriction fragment length polymorphism-based "enriched PCR" technique," Clin Cancer Res. 4(2):361-71.

Behn et al. (1998) "Sensitive detection of p53 gene mutations by a 'mutant enriched' PCR-SSCP technique," Nucleic Acids Res. 26(5):1356-8.

Behn et al. (1998) "Simple and reliable factor V genotyping by PNA-mediated PCR clamping," Thromb Haemost. 79(4):773-7.

Bertario et al (1999) "Risk of Colorectal Cander Following Colonoscopic Polypectomy" Tumori, 85:157-162.

Beskin et al. (1995) "On the Mechanism of the Modular Primer Effect," Nucleic Acids Research, vol. 23, No. 15, ppo 2881-2885.

Blum H.E., (1995) "Colorectal Cancer: Future Population Screening for Early Colorectal Cancer" European Journal of Cancer, vol. 31A, pp. 1369-1372.

Bohm et al, (1997) Int. J. Cancer (Pred. Oncol.) 74:291.

Boom et al. (1990) "Rapid and Simple Method for Purification of Nucleic Acids," Journal of Clinical Microbiology, vol. 28, No. 3, pp. 495-503.

Bos et al, (1987) "Prevalence of ras Gene Mutations in Human Colorectal Cancers" Nature vol. 327, pp. 293-297.

Botstein et al. (1985) "Strategiesand Applications of in vitro Mutagenesis," Science, 229(4719):1193-1201.

Boynton et al. (2003) "DNA integrity as a potential marker for stool-based detection of colorectal cancer," Clinical Chemistry, 49(7):1058-1065.

Braun et al, (1997) "Improved Analysis of Microsatellites Using Mass spectrometry" Genomics, vol. 46, pp. 18-23.

Brenner et al. (2005) "Fecal DNA Biomarkers for the Detection of Colorectal Neoplasia: Attractive, but is it feasible?" Journal of the National Cancer Institute, 97(15):1107-1109.

Brochure (undated) "Genotyping on the Tm/Luminex Universal Array Platform Using Primer Extension Chemistry," Tm Bioscience Corporation Technical Bulletin—403, six pages, Accessed 2002.

Burbee et al. (2001) "Epigenetic inactivation of RASSF1A in lung and breast cancers and malignant phenotype suppression," J Natl Cancer Inst. 93(9):691-9.

Caetano-Anolles "Amplifying DNA with Arbitrary Oligonucleotide Primers," Cold Spring Harbor Laboratory Press, ISSN 1054-9803, pp. 85-94 (1993).

Caldas et al. (1994) "Detection of K-ras Mutations in the Stool of Patients with Pancreatic Adenocarcinoma and Pancreatic Ductal Hyperplasia" Cancer Research, vol. 54, pp. 3568-3573.

Capozzi et al. (1999) Evaluation of the Replication Error Phenotype in Relation to Molecular and Clinicopaihological Features in Hereditary and Early Onset Colorectal Cancee European Journal of Cancer 35:289-295.

Carothers et al. "Point Mutation Analysis in a Mammalian Gene: Rapid Preparation of Total RNA, PCR Amplification of cDNA, and Taq Sequencing by a Novel Method," 494 BioTechniques, vol. 7, pp. 494-499 Abstract only, (1989).

Cave et al. (1994) "Reliability of PCR Directly from Stool Samples: Usefulness of an Internal Standard," BioTechniques, vol. 16, No. 5, pp. 809-810.

Chambers et al. (1986) "The structure of the mouse glutathione peroxidase gene: the selenocysteine in the active site is encoded by the 'termination' codon, TGA" EMBO Journal 5(6):1221-1227. Abstract only.

Chapelle (1999) "Testing Tumors for Microsatellite Instability" European Journal of Human Genetics 7:407-408.

Charlesworth et al. (Sep. 15, 1994) "The Evolutionary Dynamics of Repetitive DNA in Eukaryotes," Nature, vol. 371, pp. 215-220.

Chen et al. (1985) "Supercoil Sequencing: A Fast and Simple Method for Sequencing Plasmid DNA" DNA, 4(2):165-170.

Chen et al. (1997) "Fluorescence Energy Transfer Detection as a Homogeneous DNA Diagnostic Method," Proc. Natl Acad. Sci., vol. 97, pp. 10756-10761.

Chen et al. (1997) "Microsatellite Instability in Sporadic-Colon-Cancer Patients With and Without Liver Metastases" International Journal of Cancer, 74:470-474.

Chen et al. (1997) "Template-Directed Dye-Terminator Incorporation (TDI) Assay: A Homogeneous DNA Diagnostic Method Based on Fluorescence Resonance Energy Transfer," Nucleic Acids. Research, vol. 25, No. 2, pp. 347-353.

Chen et al. (2005) "Detection in fecal DNA of colon cancer-specific methylation of the nonexpressed vimentin gene," J Natl Cancer Inst. 97:1124-1132.

Coughlin et al. (1999) "Public Health Perspectives on Testing for Colorectal Cancer Susceptibility Genes" American Journal of Preventive Medicine, 16:99-104.

Cunningham C. and M.G. Dunlop, (1996) "Molecular Genetic Basis of Colorectal Cancer Susceptibility," British Journal of Surgery vol. 83, pp. 321-329.

Dallol et al. (2004) "RASSF1A interacts with microtubule-associated proteins and modulates microtubule dynamics," Cancer Res. 64(12):4112-6.

Dammann et al. (2000) "Epigenetic inactivation of a RAS association domain family protein from the lung tumour suppressor locus 3p21. 3."Nat Genet. 25(3):315-9.

Deng et al., (1996) "Loss of Heterozygosity in Normal Tissue Adjacent to Breast Carcinomas," Science. vol. 274, pp. 2057-2059.

Deuter et al. (1995) "A Method for Preparation of Fecal DNA Suitable for PCR," Nucleic Acids Research, vol. 23, No. 18, pp. 3800-3801.

Dib et al. (1996) "A Comprehensive Genetic Map of the Human Genome Based on 5,264 Microsatellites," Nature vol. 380, pp. 152-154.

Downward (2002) "Targeting RAS signalling pathways in cancer therapy," Nat Rev Cancer. 3(1):11-22.

Downward (2003) "Cell biology: metabolism meets death," Nature. 424(6951):896-7.

Downward (2003) "Role of receptor tyrosine kinases in G-protein-coupled receptor regulation of Ras: transactivation or parallel pathways?" Biochem J. 376(Pt 3):e9-10.

Dreijerink et al. (2001) "The candidate tumor suppressor gene, RASSF1A, from human chromosome 3p21.3 is involved in kidney tumorigenesis," Proc Natl Acad Sci USA, 98(13):7504-9.

Driscoll el aL (1989) "An In Vitro System for the Editing of Apolipoprotein B mRNA" Cell, 58:519-525.

Duffy (1995) "Can Molecular Markers Now be Used for Early Diagnosis of Malignancy?" Clin. Chem. vol. 41, No. 10, pp. 1410-1413.

Eckfeld et al. (2004) "RASSF4/AD037 is a potential ras effector/tumor suppressor of the RASSF family," Cancer Res. 64(23):8688-93.

Eguchi et al. (1996) "Mutations of the p53 Gene in the Stool of Patients with Resectable Colorectal Cancer," Cancer Supplement, vol. 77, No. 8, pp. 1707-1710.

Enari et al. (1998) "A Caspase-Activated DNase that Degrades DNA During Apoptosis, and its Inhibitor ICAD," Nature, vol. 391, pp. 43-50.

Endoh et al. (2005) "RASSF2, a potential tumor suppressor, is silenced by CpG island hypermethylation in gastric cancer," British Journal of Cancer, 93:1395-1399.

England et al. (1978) "3'-Terminal labeling of RNA with T4 RNA ligase," Nature 275:560-561.

Erickson et al.(2001) "One base sequencing (OBS): an improved method for accurate SNP scoring," Human Genome Meeting (HGM).

Erster et al, (1988) "Use of Rnase H and primer extension to analyze RNA splicing," Nucleic Acids Res., 16(13):5999-6014.

European Search Report for EP Application 09167115.6 dated Sep. 16, 2009.

Fabian et al,. (1989) "Allele-specific expression of the murine Ren-1 genes," J. Biol. Chem. 264(29):17589-17594.

Fearon (1995) "16 Molecular Abnormalities in Colon and Rectal Cancer," The Molecular Basis of Cancer, pp. 340-357.

Fearon et al. (1990) "A genetic model for colorectal tumorigenesis," Cell. 61(5):759-67.

Feng et al. (2006) "Molecular Biomarkers for Cancer Detection in Blood and Bodily Fluids," Critical Reviews in Clinical Laboratory Sciences, 43(5-6):497-560.

Fournie et al. (1995) "Plasma DNA as a Marker of Cancerous Cell Death. Investigations in Patients Suffering from Lung Cancer and in Nude Mice Bearing Human Tumours," Cancer Letters, 91:221-227.

Frangi et al. (1991) "Nonsense Mutations Affect CI Inhibitor Messenger RNA Levels in Patients with Type I Hereditary Angioneurotic Edema," J. Clinical Invest. 88:755-759.

Fu et al. (1995) "A DNA Sequencing Strategy That Requires Only Five Bases of Known Terminal Sequence for Priming," Proc. NatL Acad Sci. USA, 92: pp. 10162-10166.

Galinsky et al. (1988) "Molecular cloning and sequence analysis of the human parainfluenza 3 virus gene encoding the L protein," Virology, 165(2):499-510.

Gao et al. (1988) "Restriction primer extension method of labeling oligonucleotide probes and its application to the detection of Hb E genes," Hemoglobin, 12(5-6):691-697.

Gardner et al. (2002) "Acyclic and dideoxy terminator preferences denote divergent sugar recognition by archaeon and Taq DNA polymerases," Nucleic Acids Research, 30(2):605-613.

Giacona et al. (1998) "Cell-Free DNA in Human Blood Plasma: Length Measurements in Patients with Pancreatic Cancer and Healthy Controls," Pancreas, vol. 17, No. 1, pp. 89-97.

Gismondi et al. (1997) "Characterization of 19 Novel and Sic Recuroing APC Mutations in Italian Adenomatous Polyposis Patients, Using TWO-Different Mutation Detection Techniques" Human Mutation, vol. 9, No. 4, pp. 370-373.

Godson, (1980) "Primed synthesis methods of sequencing DNA and RNA," Fed. Proc.. 39(10):2822-2829.

Green et al. (1980) "Targeted deletions of sequences from closed circular DNA," Proc. Natl. Acad. Sci. 77(5):2455-2459.

Greene et al. (2001) "A Novel Method for SNP Analysis Using Fluorescence Polarization," Perkin Elmer Life Sciences.

Grossman et al. (1988) "Colonoscopic Screening of persons With Suspected Risk Factors for Colon Cancer" Gastmenterologv 94:395-400.

Gyllensten et al. (1995) "Sequencing of In Vitro Amplified DNA," Recombinant DNA Methodology II, (Wu, ed.) pp. 565-578.

Hasegawa et al. (1995) "Detection of K-ras Mutations in DNAs Isolated From Feces of Patients with Colorectal Tumors by Mutant-Allele-Specific Amplification (MASA)" Oncogene, vol. 10, pp. 1441-1445.

Herman (2002) "Hypermethylation pathways to colorectal cancer. Implications for prevention and detection," Gastroenterol Clin North Am. 31(4):945-58.

Herman JG, et al. (1996) "Methylation-specific PCR: A novel PCR assay for methylation status of CpG islands," Proc Natl Acad Sci USA 93:9821-9826.

Hesson et al. (2003) "NORE1A, a homologue of RASSF1A tumour suppressor gene is inactivated in human cancers," Oncoqene. 22(6):947-54.

Hesson et al. (2004) "Frequent epigenetic inactivation of RASSF1A and BLU genes located within the critical 3p21.3 region in gliomas," Oncogene 23(3):2408-19.

Hesson et al. (2005) "CpG island promoter hypermethylation of a novel Ras-effector gene RASSF2A is an early event in colon carcinogenesis and correlates inversely with K-ras mutations," Oncogene 24:3987-3994.

Hickman et al. (1994) "Apoptosis and cancer chemotherapy," Phil. Trans R. Soc. Lond., 345:319-325.

Hoang et al. (1997) "BAT-26, an Indicator of the Replication Error Phenotype in Colorectal Cancers and Cell Lines" Cancer Research 57: 300-303.

Hollstein et al. (1991) "p53 Mutations in Human Cancers," Science, vol. 253, pp. 49-53.

Honchel et al. (1995) "Genomic Instability in Neoplasia," Seminars in Cell Biology, vol. 6, pp. 45-52.

Hornes et al. (1990) "Emerging Techniques: Magnetic DNA Hybridization Properties of Oligonucleotide Probes Attached to Superparamagnetic Beads and Their Use in the Isolation of Poly(A) mRNA From Eukaryotic Cells," GATA 7(6):145-150.

Hoss et al. (1992) "Excrement Analysis by PCR" Scientific Correspondence pp. 199.

Hunkapiller et al. (1984) "A microchemical facility for the analysis and synthesis of genes and proteins," Nature 310:305-311.

Iacopetta et al. (1998) "Rapid and Nonisotopic SSCP-based Analysis of the BAT-26 Mononucleotide Repeat for Identification of the Replication Error Phenotype in Human Cancers," Human Mutation 12:355-360.

Iino et al. (1999) "DNA Microsatellite Instability in Hyperplastic Polyps, Serrated Adenomas, and Mixed Polyps: a Mild Mutator Pathway for Colorectal Cancer?" Journal of Clinical Pathology 52: 5-9.

Ikonen et al. (1992) "Quantitative Determination of Rare mRNA Species by PCR and Solid-phase Minisequencing," Cold Spring Harbor Laboratory Press, ISSN 1054-8903, pp. 234-240.

Iniesta et al. (1998) "Genetic Abnormalities and Microsatellite Instability in Colorectal Cancer" Cancer Detection and Prevention 22:383-395.

International Search Report for PCT/US99/08849 (Sep. 13, 1999).
International Search Report for PCT/US03/04827 (Sep. 4, 2003).
International Search Report for PCT/US05/016518, (Apr. 7, 2006).
International Search Report for PCT/US05/30942, (Jul. 26, 2006).
International Search Report for PCT/US05/39670 (Apr. 12, 2006).

Irimia et al. (2004) "CpG island promoter hypermethylation of the Ras-effector gene NORE1 A occurs in the context of a wild-type K-ras in lung cancer," Oncogene. 23(53):8695-9.

Ishimaru et al. (1995) "Microsatellite Instability in Primary and Metastatic Colorectal Cancers" International Journal of Cancer 64:153-157.

Iwaya et al. (1998) "Infrequent Frateshift Mutations of Polynucleotide Repeats in Multiple Primary Cancers Affecting the Esophagus and Other Organs" Genes, Chrom & Cancer 23:317-322.

Jack et al. (2002) "Kicking the Sugar Habit: AcyNTP Terminator Incorporation by Vent DNA Polymerase" HGH2002 Poster Abstracts: 12. New Technologies, Poster No. 621, Abstract only.

Jarvinen et al. (1995) "Screening Reduces Colorectal Cancer Rate in Families With Hereditary Nonpolyposis Colorectal Cancer" Gastroenterology 108: 1405-1411.

Jeffreys et al. (2003) "DNA enrichment by allele-specific hybridization (DEASH): a novel method for haplotyping and for detecting low-frequency base substitutional variants and recombinant DNA molecules," Genome Research, 13:2316-2324.

Jernvall et al. (1999) "Microsatellite Instability: Impact on Cancer Progression in Proximal and Distal Colorectal Cancers" European Journal of Cancer 35:197-201.

Jessup et al. (1992) "The Biology of Colorectal Carcinoma," Current Problems in Cancer pp. 263-328.

Jonsson et al. (1995) "From Mutation Mapping to Phenotype Cloning," Proc. Natl. Acad. Sci., vol. 92 pp. 83-85.

Kainz et al. (1989) "A modified primer extension procedure for specific detection of DNA-RNA hybrids on nylon membranes," 179(2):366-370, Abstract only.

Kawakami et al. (2000) "Hypermethylated APC DNA in Plasma and Prognosis of Patients with Esophageal Adenocarcinoma," Journal of the National Cancer Institute, 92(22):1805-1811.

Khokhlatchev et al. (2002) "Identification of a novel Ras-regulated proapoptotic pathway," Curr Biol. 12(4):253-65.

Kieleczawa et al. (1992) "DNA Sequencing by Primer Walking with Strings of Contiguous Hexamers," Science,258: pp. 1787-1791.

Kim et al. (2006) "CpG island methylation of genes accumulates during the adenoma progression step of the multistep pathogenesis of colorectal cancer," Genes Chromosomes Cancer 45:781-789.

Kim et al. (1998) Microsatellite Instability in Young Patients With Colorectal Cancee Pathology International 48: 586-594.

Ko et al. (1999) "Genomic Instability and Alterations in Apc, Mcc and Dcc in Hong Kong Patients with Colorectal Carcinoma," Int. J. Cancer (Pred. Oncol.1, 84:404-409.

Komher at al. (1989) "Mutation detection using nucleotide settings that alter electrophoretic mobility," Nucleic Acids Research, 17(19):7779-7784.

Kondo et al. (2004) "Epigenetic changes in colorectal cancer," Cancer Metastasis Rev. 23(1-2):29-39.

Konishi et al. (1996) "Molecular Nature of Colon Tumors in Hereditary Nonpolyposis Colon Cancer, Familial Polyposis, and Sporadic Colon Cancer" Gastroenterology 1 1 I: 307-317.

Kotler et al, (1993) "DNA Sequencing: Modular Primers Assembled from a Library of Hexamers or Pentamers," Proc. Natl. Acad Sci. USA, 90: pp. 4241-4245 (May 1993).

Krook et al. (1992) "Rapid and simultaneous detection of multiple mutations by pooled and multiplex single nucleotide primer extension: application to the study of insulin-responsive glucose transporter and insulin receptor mutations in non-insulin-dependent diabetes," Human Molecular Genetics, vol. 1, No. 6, pp. 391-395.

Kuppuswamy et al. (1991) "Single Nusleotide primer extension to detect genetic diseases: Experiemental application to hemophilia B (factor IX) and Cystic fibrosis genes," Proc. Natl. Acad. Sci., 88:1143-1147.

Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" Gut 44:839-843.

Lebacq (1992) "Polymerase chain reaction and other methods to detect hot-spot and multiple gene mutations," Advances in Clinical Biology, vol. 50, pp. 709-712.

Lee et al, (1992) DNA sequencing with dye-labeled terminators and T7 DNA polymerase: effect of dyes and dNTPs on incorporation of dye-terminators.

Lengauer et al. (1998) "Genetic Instabilities in Human Cancers," Nature, vol. 396, pp. 643-649.

Leong et al. (1993) "Detection of MYCN Gene Amplification and Deletions of Chromosome Ip in Neuroblastoma by In Situ Hybridization Using Routine Histologic Sections," Laboratorv Investigations, vol. 69, No. 1, pp. 43-50.

Lerman et al. (2000) "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium," Cancer Res. 60(21):6116-33.

Lin et al. (1998) "Colorectal and Extracolonic Cancer Variations in MLHI/MSH2 Hereditary Nonpolyposis Colorectal Cancer Kindreds and the General Population" Diseases of the Colon & Rectum 41:428-433.

Lipkin et al. (1998) "Quantitative Trait Locus Mapping in Dairy Cattle by Means of Selective Milk DNA Pooling Using Dinucleotide Microsatellite Markers: Analysis of Milk Protein Percentage" Genetics 49:1557-1567.

Litia et al. (1992) "Simultaneous Detection of Two-Cystic Fibrosis Alleles Using Dual-Label Time-Resolved Fluorometry," Molecular and Cellular Probes, vol. 6, pp. 505-512.

Liu et al. (2003) "Control of microtubule stability by the RASSF1 A tumor suppressor," Oncogene. 22(50):8125-36.

Liu et al. (1986) "Synthesis of a fixed-length single-stranded DNA probe by blocking primer extension in bacteriophage M13," Gene, 42:113-117.

Lleonart et al. (1998) "Microsatellite Instability and p53 Mutations in Sporadic Right and Left Colon Carcinoma" American Cancer Society 83:889-895.

Lo et al. (1984) "Specific amino acid substitutions in bacterioopsin: Replacement of a restriction fragments containing altered codons," Proc. Natl. Acad. Sci., 81:2285-2289.

Loktionov A. and I. K. O'Neill, (1995) "Early Detection of Cancer-Associated Gene Alterations in DNA Isolated from Rat Feces During Intestinal Tumor Induction with 1,2-Dimethylhydrazine," International Journal of Oncology, vol. 6, pp. 437-445.

Loktionov et al. (1998) "Quantitation of DNA from Exfoliated Colonocytes Isolated from Human Stool Surface as a Novel Noninvasive Screening Test for Colorectal Cancer," Clinical Cancer Research, vol. 4, pp. 337-341.

Lothe, et al. (1998) "The APC Gene 11307K Variant is Rare in Norwegian Patients with Familial and Sporadic Colorectal or Breast Cancer" Cancer Research, vol. 58, pp. 2923-2924.

Luo et al. (1988) "Point mutations in glycoprotein gene of vesicular stomatitis virus (New Jersey serotype) selected by resistance to neutralization by epitope-specific monoclonal antibodies," Virology, 163(2):341-348.

Makristathis et al. (1998) "Detection of Helicobacter pylori in Stool Specimens by PCR and Antigen Enzyme Immunoassay," Journal of Clinical Microbiology, vol. 36, No. 9, pp. 2772-2774.

Mao L. et al. (1996) "Molecular Detection of Primary Bladder Cancer by Microsatellite Analysis," Science. vol. 271, pp. 659-662.

Matteucci et al. (1981) "Studies on Nucleotide Chemistry IV. Synthesis of Deoxyoligonucleotides on a Polymer Support," J. Am. Chem. Soc., 103:3185-3191.

Maxam et al. (1977) "A new method for sequencing DNA," Proc. Natl. Acad. Sci., 74(2):560-564.

Medeiros et al. (1989) "M13 Bioprints: non-isotopic detection of individual-specific human DNA fingerprints with biotinylated M13 bacteriophage," Forensic Sci. Int., 43(3):275-280.

Meijers-Heijboer et al. (1999) "Familial Endometrial Cancer in Female Carriers of MSH6 Germline Mutations" Nature Genetics 23: 142-144.

Miller et al. (1997) "Semiautomated Resolution of Overlapping Stutter Patterns in Genomic Microsatellite Analysis" Analytical Biochemistry 251:50-56.

Mills, Stacey E. (2001) "Digital Diagnoses in an Analog World," American Society for Clinical Pathology Editorial, two pages.

Morinaga et al. (1984) "Improvement of Oligonucleotide-Directed Site-Specific Mutagenesis Using Double-Stranded Plasmid DNA," Biotechnology pp. 636-639.

Muller et al. (2004) "Methylation changes in faecal DNA: a marker for colorectal cancer screening?" Lancet. 363(9417):1283-5.

Myers, R.M. (1993) "The Pluses of Subtraction," Science. vol. 259, pp. 942-943.

Naber (1994) "Molecular Pathology—Detection of Neoplasia," New England Journal of Medicine, vol. 331, No. 22, pp. 1508-1510.

Netzer, P. et al. (1997) "Screening sigmoidoscopy or colosopy for detection of colorectal adenomas and cancers?" Gastroenterology, 112(4):A626, Bibliographic data only.

Nikiforov et al. (1994) "Genetic Bit Analysis: a solid phase method for typing single nucleotide polymorphisms," Nucleic Acids Research, vol. 22, No. 20, pp. 4167-4175, Abstract only.

Nollau et al. (1996) "Detection of K-ras Mutations in Stools of Patients with Colorectal Cancer by Mutant-Enriched PCR," Int. J. Cancer, vol. 66 pp. 332-336.

Nollau et al. (1996) "Isolation of DNA from Stool and Bodily Fluids for PCR Amplication," BioTechniques, vol. 20, No. 5, pp. 784-788.

Olsen et al. (1989) "Incomplete primer extension during in vitro DNA amplification catalyzed by Taq polymerase; exploitation for DNA sequencing," Nucleic Acids Res.. 17(23):9613-9620, Abstract only.

Olson et al. (2005) "DNA stabilization is critical for maximizing performance of fecal DNA based colorectal cancer tests," Diaqn Mol Pathol 14:183-191.

Orlow et al. (1995) "Deletion of the p16 and p15 Genes in Human Bladder Tumors Journal of the National Cancer Institute,," vol. 87, No. 20, pp. 1524-1529.

Ortiz-Vega et al. (2002) "The putative tumor suppressor RASSF1 A homodimerizes and heterodimerizes with the Ras-GTP binding protein Nore1," Oncogene. 21(9):1381-90. Erratum in: Oncogene 21(12):1943.

Palmieri et al. (1999) "Polymerase Chain Reaction-Based Detection of Circulating Melanoma Cells as an Effective Marker of Tumor Progression," Journal of Clinical Oncology, 17(1): 304-311.

Park et al.(1999) "Gene-Environment Interaction in Hereditary Nonpolyposis Colorectal Cancer with Implications for Diagnosis and Genetic Testing" International Journal of Cancer 82: 516-519.

Parker et al. (1988) "Interaction of 2-Halogenated dATP analogs (F, Cl and Br) with human DNA polymerases, DNA primase, and ribonucleotide reductase," Mol. Pharmacol., 34(4):485491, Abstract only.

Peattie, (1979) "Direct chemical method for sequencing RNA," Proc. Natl. Acad. Sci., 76(4):1760-1764.

Peltomaki et al (1997) "Mutations Predisposing to Hereditary Nonpolyposis Colorectal Cancer: Database and Results of a Collaborative Study" Gastroenterology 113: 1146-1158.

Perlin et al. (1995) "Toward Fully Automated Tenotyping: Genotyping Microsatellite Markers by Deconvolution" American Journal of Human Genetics 57:1199-1210.

Pharmacia (1991/1992) Molecular and Cell Biology Catalogue, pp. 8.3-8.6.

Pharmacia (1998) BioDirectorv, pp. 104-109.

Piao et al. (1997) "Relationship between Loss of Heterozygosity of Tumor Suppressor Genes and Histologic Differentiation in Hepatocellular Carcinoma," Cancer, vol. 80, No. 5, pp. 865-872.

Ponz de Leon et al. (1998) "Frequency and Type of Colorectal Tumors in Asymptomatic High Risk Individuals in Families with Hereditary Nonpolyposis Colorectal Cancer" Cancer Epidemiology, Biomarkers & Prevention 7: 639-641.

Ponz de Leon et al. (1999) "Hereditary Colorectal Cancer in the General Population: From Cancer Registration to Molecular Diagnosis" Gut 45: 32-38.

Praskova et al. (2004) "Regulation of the MST1 kinase by autophosphorylation, by the growth inhibitory proteins, RASSF1 and NORE1, and by Ras," Biochem J. 381(Pt 2):453-62.

Prober et al. (1987) "A System for Rapid DNA Sequencing with Fluorescent Chain-Terminating Dideoxynucleotides," Research Articles, pp. 336-341.

Pyatt et al. (1999) "Polymorphic Variation at the BAT-25 and BAT-26 Loci in Individuals of African Origin" American Journal of Pathology 155: 349-353.

Raff (1998) "Cell Suicide for Beginners," Nature, vol. 396, pp. 119-122.

Rashid et al. (1999) "Genetic Epidemiology of Mutated K-ras Proto-Oncogene, Altered Suppressor Genes, and Microsatellite Instability in Colorectal Adenomas" Gut 44: 826-833.

Ravelingien et al. (1995) "Contribution of Molecular Oncology in the Detection of Colorectal Carcinomas," Acta Gastro-Enterologica Belgic a, vol. 58, pp. 270-273.

Rhyu (1996) Molecular Mechanisms Underlying Hereditary Nonpolyposis Colorectal Carcinoma, Journal of the National Cancer Institute, vol. 88, No. 5, pp. 240-251.

Rice et al. (2001) "Identification of single nucleotide polymorphisms (SNPs) and other sequence changes and estimation of nucleotide diversity in coding and flanking regions of the NMDAR1 receptor gene in schizophrenic patients," Molecular Psychiatry, 6(3):274-284.

Ridanpaa et al. (1995) Detection of Loss of Heterozygosity in the p53 Tumor Suppressor Gene Using a PCR-based Assay, Path. Res. Pract., vol. 191, pp. 399-402.

Riegler et al. (1999) "Prevalence of HNPCC in a Series of Consecutive Patients on the First Endoscopic Diagnosis of Colorectal Cancer: A Multicenter Study" Endoscopy 31: 337-341.

Rinaldy et al. (1988) "Gene Cloning Using cDNA Libraries in a Differential Competition Hybridization Strategy: Application to Cloning XP-A Related Genes," DNA 7(8):563-70.

Rodriguez-Bigas et al. (1997) "A National Cancer Institute Workshop on Hereditary NonpolyposisColorectal Cancer Syndrome: Meeting Highlights and Bethesda Guidelines" Journal of the National Cancer Institute 89:1758-1762.

Roemer et al (2000) "Sequencing BAC DNA With Near-Infrared Flourescent Non-Nucleotide Terminators," LI-COR On-line Poster 530, LI-COR, Inc., Biotechnology, Lincoln, Nebraska, nine pages.

Rosenthal et al. (1985) "Solid-phase methods for sequencing of nucleic acids, I. Simultaneous sequencing different oligodeoxyribonucleotides using a new, mechanically stable anion-exchange paper," Nucleic Acids Research, 13(4):1173-1184.

Runnebaum et a. (1994) "Multiplex PCR Screening detects small p53 deletions and insertions in human ovarian cancer cell lines," Human Genetics, vol. 93, pp. 620-624.

Salahshor et al. (1999) "Microsatellite Instability in Sporadic Colorectal Cancer is Not an Independent Prognostic Facto(" British Journal of Cancer 81: 190-193.

Sambrook et al. (1989) "Molecular Cloning," Second Edition, p. 13.67-13.69.

Samiotaki et al. (1994) "Dual-Color Detection of DNA Sequence Variants by Ligase-Mediated Analysis," Genomics 20:238-42.

Samowitz et al. (1995) "Microsatellite Instability in Human Colonic Cancer Is Not a Useful Clinical Indicator of Familial Colorectal Cancer" Gastroenterology 109: 1765-1771.

Samowitz et al. (1997) "Microsatellite Instability in Colorectal Adenomas" Gastroenterology 112: 1515-1519.

Samowitz et al. (1999) "BAT-26 and BAT-40 Instability in Colorectal Adenomas and Carcinomas and Germline Polymorphisms" American Journal of Pathology 154:1637-1641.

Samuels et al. (2004) "High frequency of mutations of the PIK3CA gene in human cancers," Science, 304(5670):554.

Sanger et al. (1975) "A Rapid Method for Determing Sequences in DNA by Primed Synthesis with DNA Polymerase" J. Mol. Biol.. 94:441-448.

Sanger et al. (1977) "DNA Sequencing with Chain-Terminating Inhibitors" Proc. Natl. Acad. Sci. USA, vol. 74, No. 12, pp. 5463-5467.

Segel (1976) "Double Label Analysis," Biochemical Calculations, 2d ed., pp. 373-376.

Sheehan et al. (1987) "Reducing agent-sensitive dimerization of the hemagglutinin-neuraminidase glycoprotein of Newcastle disease virus correlates with the presence of cycteine at residue 123," Virology, 161(2):603-606.

Shitoh et al. (1998) "Important Microsatellite Markers in the Investigation of RER in Colorectal Cancers," Jim. J. Cli, Oncol vol. 28, No. 8, pp. 538-541.

Shivakumar et al. (2002) "The RASSF1A tumor suppressor blocks cell cycle progression and inhibits cyclin D1 accumulation," Mol Cell BioL 22(12):4309-18.

Shortle et al, (1980) "Segment-directed mutagenesis: Construction in vitro of point mutations limited to a small predetermined region of a circular DNA molecule," Proc. Natl. Acad. Sci., 77(9):5375-5379.

Shortle . (1981) "Directed Mutagenesis," Ann. Rev. Genet. 15:265-294.

Shortle et al. (1982) "Gap misrepair mutagenesis: Efficient site-directed induction of transition, transversion, and frameshift mutations in vitro," Proc. Natl. Acad. Sci., 79:1588-1592.

Shumaker et al. (1996) "Mutation Detection by Solid Phase Primer Extension," Human Mutation, vol. 7, pp. 346-354.

Sidransky et al. (1992) "Identification of ras Oncogene Mutations in the Stool of Patients with Curable Colorectal Tumors," Science, vol. 256, pp. 102-105.

Singer et al. (1989) "Effect of 3' flanking neighbors on kinetics of pairing of dCTP or dTTP opposite O6-methylguanine in a defined primed oligonucleotide when *Escherichia coli* DNA polymerase I is used," Proc. Natl. Acad. Sci., 86:8271-8274.

Singer-sam et al. (1992) "A Sensitive, Quantitative Assay for Measurement of Allele-specific Transcripts Differing by a Single Nucleotide," PCR Methods and Applications. 1:160-163.

Smith-Ravin et al. (1995) "Detection of c-Ki-ras Mutations in Fecal Samples from Sporadic Colorectal Cancer Patients," Gut, vol. 36, pp. 81-86.

Sokolov, (1989) "Primer extension technique for the detection of single nucleotide in genomic DNA,"Nucleic Acids Research, 18(12):3671.

Srinivas et al. (2001) "Trends in biomarker research for cancer detection," The Lancet, 2: 698-704.

Stahl et al. (1988) "Solid phase DNA sequencing using the biotin-avidin system," Nucleic Acids Research, 16(7):3025-3038.

Suzuki et al. (2002) "A genomic screen for genes upregulated by demethylation and histone deacetylase inhibition in human colorectal cancer," Nat Genet 31(2):141-9. Epub May 6, 2002.

Syngal et al. (1998) "Benefits of Colonoscopic Surveillance and Prophylactic Colectomy in Patients With Hereditary Nonpolyposis Colorectal Cancer Mutations," Annals of Internal Medicine 129: 787-796.

Syngal et al. (1999) "Interpretation of Genetic Test Results for Hereditary Nonpolyposis Colorectal Cancer" JAMA 282: 247.

Syvanen (1994) Detection of Point Mutations in Human Genes by the Solid-phase Minisequencing Method, Clinica Chimica Acta, vol. 226, Abstract Only.

Syvanen et al. (1990) "A primer-Guided Nucleotide Incorporation Assay in the Genotyping of Apolipoprotein E," Genomics, 8:684-692.

Syvänen, (1997) "Solid-Phase Minisequencing," Detection of Mutations and Polymorphisms in DNA, Chapter 6, pp. 53-64.

Tagore et al. (2003) "Sensitivity and Specificity of a Stool DNA Multitarget Assay Panel for the Detection of Advanced Neoplasia," Clinical Colorectal Cancer, 3(1):47-53.

Takeda et al. (1993) "Detection of K-ras Mutation in Sputum by Mutant-Allele-Specific Amplification (MASA)" Human Mutation, vol. 2, pp. 112-117.

Thibodeau et al. (1993) "Microsatellite Instability in Cancer of the Proximal Colon," Science, vol. 260, pp. 816-819.

Thiede et al. (1996) "Simple and sensitive detection of mutations in the ras proto-oncogene using PNA-mediated PCR clamping," Nucleic acids research, 24:983-984.

Tommasi et al. (2002) "RASSF3 and NORE1: identification and cloning of tWO-human homologues of the putative tumor suppressor gene RASSF1" Oncogene. 21(17):2713-20.

Toyota et al. (1999) "CpG island methylator phenotype in colorectal cancer," Proc Nat Acad Sci USA 96:8681-8686.

Traverso et al. (2002) "Detection of APC Mutations in Fecal DNA from Patients with Colorectal Cancer," N Engl. J. Med.. 346(5):311-320.

Ugozzoli, et al. (1992) "Detection of Specific Alleles by Using Allele-Specific Primer Extension Followed by Capture on Solid Support," CATA 9(4): pp. 107-112.

van Engeland et al. (2002) "K-ras mutations and RASSF1A promoter methylation in colorectal cancer," Oncogene. 21(23):3792-5.

Vasen et al. (1993) "Surveillance in Hereditary Nonpolyposis Colorectal Cancer: An International Cooperative Study of 165 Families" Diseases of the Colon & Rectum) 36:1-4.

Vasen et al. (1998) "A Cost-Effectiveness Analysis of Colorectal Screening of Hereditary Nonpolyposis Colorectal Carcinoma Gene Carriers" American Cancer Society 82:1632-1637.

Vasen et al. (1999) "New Clinical Criteria for Hereditary Nonpolyposis Colorectal Cancer (HNPCC, Lynch Syndrome) Proposed by the International Collaborative Group on HNPCC" Gastroenterology, 116:1453-1456.

Vavvas et al. (1998) "Identification of Nore1 as a potential Ras effector," J Biol Chem. 273(10):5439-42.

Villa et al. (1996) "Identification of Subjects at Risk for Colorectal Carcinoma Through a Test Based on K-ras Determination in the Stool," Gastroenterology, vol. 110, No. 5, pp. 1346-1353.

Vogelstein, B. And Kinzler, K.W., (1999) "Digital PCR," Proc. NatL Acad. Sci. USA, vol. 96, pp. 9236-9241.

Vos et al. (2003) "RASSF2 is a novel K-Ras-specific effector and potential tumor suppressor," J Biol Chem. 278(30):28045-51.

Vos et al. (2004) "A role for the RASSF1 A tumor suppressor in the regulation of tubulin polymerization and genomic stability," Cancer Res. 64(12).4244-50.

Vreeland et al. (2002) "Multiplexed, High-Throughput Genotyping by Single-Base Extension and End-Labeled Free-Solution Electrophoresis," Anal. Chem. 74:4328-4333.

Wada et al. (1983) "Automatic DNA sequencer: Computer-programmed microchemical manipulator for the Maxam-Gilbert sequencing method," Rev_Sci. Instrum., 54(11):1569-1572.

Wagner et al. (2002) "Frequent RASSF1A tumour suppressor gene promoter methylation in Wilms' tumour and colorectal cancer," Oncoqene. 21 (47):7277-82.

Wallace et al. (1979) "Hybridization of Synthetic Oligodeoxyribonucleotides to <DT 174 DNA: the Effect of Single Base Pair Mismatch," Nucleic Acids Research, vol. 6, No. 11, pp. 3543-3557.

Walsh et al. (1996) "Sequence Analysis and Characterization of Stutter Products at the Tetranucleotide Repeat Locus vWA," Nucleic Acids Research vol. 24, No. 14, 2807-2812.

Walsh et al. (1992) "Preferential PCR Amplification of Alleles: Mechanisms and Solutions," PCR Methods and Applications, pp. 241-250.

Wang et al. (1998) Large-Scale Identification, Mapping, and Genotyping of Single Nucleotide Olymorphism in the Human Genome, Science, vol. 280, pp. 1077-1082.

Watson et al. (1994) "Isolation of Differentiality Expressed Sequence Tags from Human Breast Cancer," Advances in Brief XP 000576043 pp. 4598-4602.

Whitney et al. (2004) "Enhanced retrieval of DNA from human fecal samples results in improved performance of colorectal cancer screening test," J Mol Diagn. 6:386-395.

Written opinion for PCT/US05/30942, (Jul. 26, 2006).

Written opinion for PCT/US05/39670 dated Apr. 12, 2006.

Young G.P., and B.H. Demediu, (1992) "The Genetics, Epidemiology, and Early Detection of Gastrointestinal Cancers" Current Opinion in Oncology, vol. 4, pp. 728-735.

Zakour et al. (1984) "Site specific mutagenesis: insertion of single noncomplementary nucleotides at specified sites by error-directed DNA polymerization," Nucleic Acids Research, 12(16):6615-6628.

Zhang et al. (2006) "Inactivation of RASSF2A by promoter methylation correlates with lymph node metastasis in nasopharyngeal carcinoma," International Journal of Cancer, 120:32-38.

Zhou et al. (1997) "Allelic Profiles of Mononucleotide Repeat Microsatellites in Control Individuals and in Colorectal Tumors With and Without Replication Errors" Oncoeene 15: 1713-1718.

Zhou et al. (1998) "Determination of the Replication Error Phenotype in Human Tumors Without the Requirement for Matching Normal DNA by Analysis of Mononucleotide Repeat Microsatellites" Genes. Chromosomes & Cancer 21: 101-107.

Zimmem et al. (1978) "3'-Terminal nucleotide sequence of encephalomyocarditis virus RNA determined by reverse transcriptase and chain-terminating inhibitors," Proc. Natl. Acad. Sci., 75:4257-4260.

Zitt et al. (2007) "DNA methylation in colorectal cancer," Disease Markers 23(1-2):51-71.

Zoller et al. (1982) "Oligonucleotide-directed mutagenesis using M13-derived vectors: an efficient and general procedure for the production of point mutations in any fragment of DNA," Nucleic Acids Research, 10(20):6487-6500.

* cited by examiner

METHOD FOR DETECTING RECOMBINANT EVENT

RELATED APPLICATIONS

This application is a national stage filing under 35 U.S.C. §371 of PCT International application PCT/US2005/030942 designating the United States of America, and filed Aug. 29, 2005, the entire contents of which are hereby incorporated herein by reference. This application claims the benefit under 35 U.S.C. §119(e) to U.S. Provisional Application No. 60/604,870, filed on Aug. 27, 2004, the entire contents of which are hereby incorporated herein by reference.

FIELD OF THE INVENTION

The invention relates to methods for isolating and detecting chimeric nucleic acid molecules in biological samples.

BACKGROUND

Due to the stochastic nature of nucleic acid amplification, mutated species of nucleic acid are often difficult to detect. For example, when a wild-type sequence is present in a sample in vast excess relative to a mutant sequence, it is statistically unlikely that the mutant sequence will be amplified using primers that span the mutation (i.e., only the wild-type templates will be amplified). This problem is compounded in the situation in which there is a recombinant event between two genes, resulting in a subpopulation of recombinant, or chimeric, nucleic acids (i.e., containing a portion of a first wild-type nucleic acid and a portion of a second wild-type nucleic acid). Amplification of the chimeric nucleic acid is complicated not only by the stochastic effects described above but also by interference from the wild-type nucleic acid. Any primers intended to amplify only one of the two segments of the chimeric nucleic acid will necessarily also amplify the corresponding wild-type nucleic acid (e.g. the full length wild-type nucleic acid), resulting in the inability to determine which amplicons come from the chimera.

SUMMARY OF THE INVENTION

Aspects of the invention relate to detecting chimeric nucleic acid molecules in biological samples. In one aspect, a chimeric nucleic acid is captured and a portion of the captured nucleic acid is amplified and detected. In certain embodiments, methods for detecting a chromosomal translocation event are provided. The presence of a chimeric nucleic acid in a biological sample obtained from a subject can be indicative of the presence of a disease in the subject. Aspects of the invention are useful to increase the yield of a chimeric nucleic acid that is present in a biological sample in a low absolute amount and/or when the chimeric nucleic acid is present in a biological sample at a low frequency relative to corresponding non-chimeric nucleic acids.

Methods of amplifying a portion of a chimeric nucleic acid in a heterogeneous sample are provided. In one embodiment, methods include the steps of exposing a sample that is suspected of including a first nucleic acid, a second nucleic acid, and a chimeric nucleic acid containing a portion of the first nucleic acid and a portion of the second nucleic acid to a capture probe capable of hybridizing to a portion of the first nucleic acid, thereby to capture the chimeric nucleic acid if it is present in the sample. The uncaptured nucleic acid may be removed from the sample, and a portion of the second nucleic acid may be amplified from the chimeric nucleic acid. In one embodiment, the presence of an amplified chimeric nucleic acid is indicative of disease. In one embodiment, the chimeric nucleic acid is a recombinant nucleic acid. In another embodiment, the chimeric nucleic acid is RNA. In yet another embodiment, RNA in the sample is purified prior to the exposing step. In a further embodiment, the method includes the step of preparing a cDNA from RNA. In another embodiment, the amplifying step selectively amplifies a portion of a second nucleic acid present in a chimeric nucleic acid. In a further embodiment, the amplifying step includes exposing a captured nucleic acid to a first primer that is complementary to a portion of a first nucleic acid and a second primer that is complementary to a second nucleic acid.

In certain embodiments, methods for detecting a chromosomal translocation event in a DNA sample are provided. Methods may include adding a DNA sample to an immobilized nucleic acid capture probe capable of hybridizing to a DNA molecule suspected of being present in the DNA sample. The DNA sample may be exposed repeatedly to the immobilized nucleic acid capture probe using reverse-field electrophoresis. The captured DNA sample may be removed from the nucleic acid capture probe and amplified. In one embodiment, the nucleic acid capture probe is immobilized on one or more beads. In another embodiment, the nucleic acid capture probe is immobilized on a gel associated with a membrane. In yet another embodiment, two or more nucleic acid capture probes are immobilized. In a further embodiment, the captured DNA sample is amplified using a PCR reaction. In another embodiment, a first primer and a second primer are present in the PCR reaction. In a further embodiment, the first primer corresponds to a region of a first chromosome. In another embodiment, the second primer corresponds to a region of a second chromosome.

The detection of one or more chimeric nucleic acids in a biological sample may be indicative of disease. In one embodiment, a heterogeneous biological sample obtained from a subject may be analyzed for the presence of a chimeric nucleic acid indicative of cancer in the subject. In another embodiment, a prenatal genetic analysis may include an assay to detect the presence of a chimeric nucleic acid in a maternal and/or fetal biological sample.

DETAILED DESCRIPTION

Figure 1:
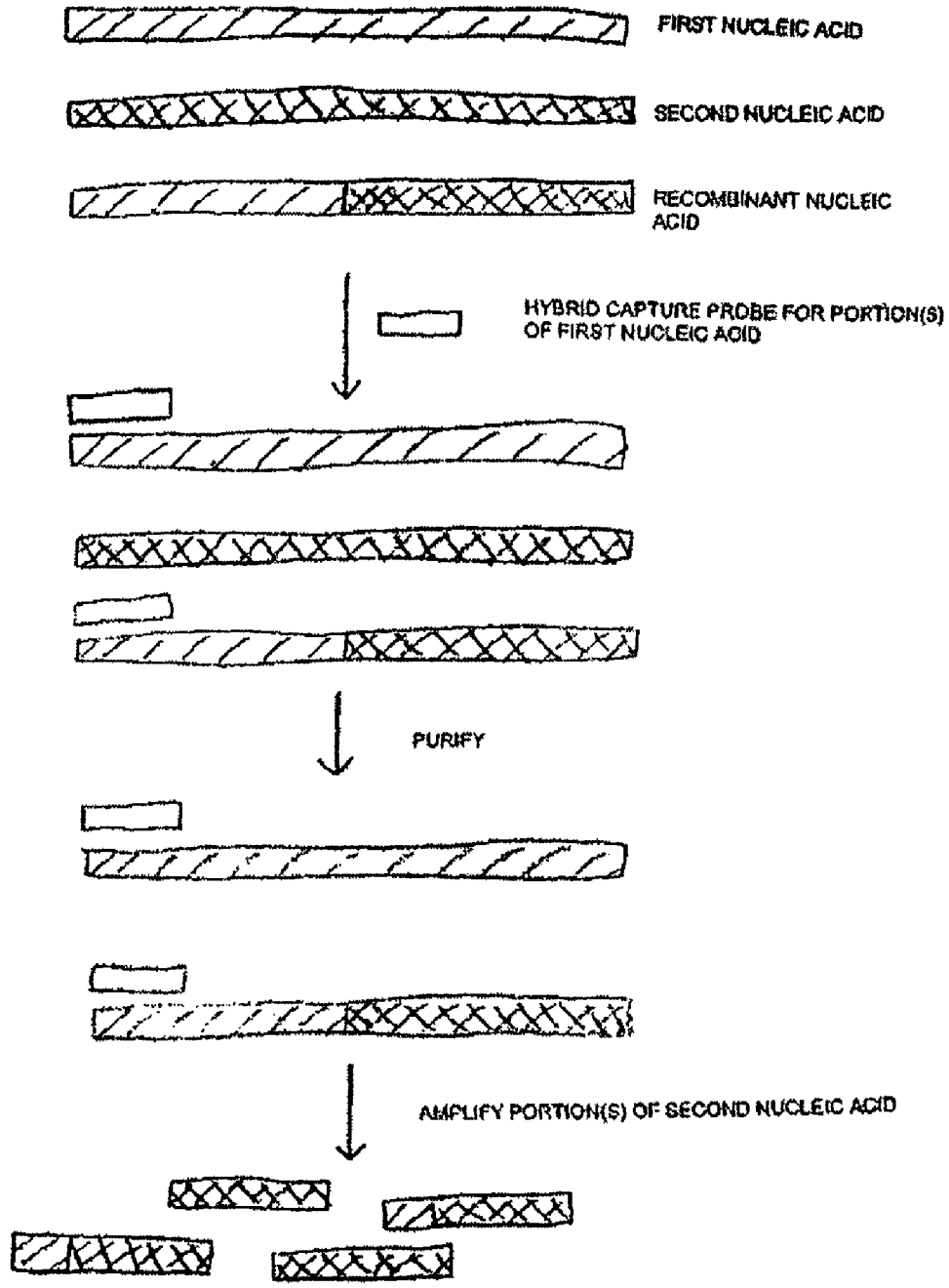
FIG. 1. Schematic diagram of the capture and analysis of DNA in a sample.

The invention provides methods for isolating and amplifying selected portions of chimeric nucleic acids from biological samples (e.g., heterogeneous biological samples). Methods of the invention may be useful for detecting indicia of one or more conditions that are associated with the presence of abnormal chimeric nucleic acids. Methods of the invention are particularly useful to detect and/or isolate abnormal chimeric nucleic acids that are present in low amounts and/or at low frequencies in biological samples. Accordingly, early indicia of certain diseases associated with the presence of chimeric nucleic acid can be detected.

In one aspect, a chimeric nucleic acid may be detected by capturing a nucleic acid molecule containing a portion of a first nucleic acid and assaying the captured nucleic acid molecule to determine whether it also contains a portion of a second nucleic acid that is not normally associated with the first nucleic acid (e.g., the first and second nucleic acids are normally on different nucleic acid molecules or chromosomes, or are normally not at close proximity on the same nucleic acid molecule or chromosome).

Methods of the invention can be used to detect chimeric nucleic acids in heterogeneous biological samples containing an excess of corresponding non-chimeric nucleic acids (e.g., normal nucleic acids). Accordingly, methods of the invention are useful to detect indicia of disease in biological samples containing an excess of normal (e.g., healthy) cells, and/or nucleic acids derived from normal cells. In certain embodiments, chimeric nucleic acid detection may be used to detect indicia of cancer (e.g., in stool, blood, plasma, serum, etc.). In certain embodiments, chimeric nucleic acid detection may be used for prenatal detection of indicia of fetal abnormalities (e.g., in chorionic villus, placental biopsies, amniotic fluid, fetal blood, fetal serum, fetal plasma, maternal blood, maternal serum, or maternal plasma, etc.).

Certain aspects of the invention provide highly sensitive assays for early disease detection by detecting small amounts of chimeric nucleic acids that are present at the early stages of certain diseases or that are present in small numbers in a biological sample. For example, early stages of cancer, pre-cancer, or adenoma may be associated with certain chromosomal rearrangements resulting in the presence of chimeric nucleic acid molecules in diseased cells. In addition, genomic instability is often associated with cancer progression. In either event, a biological sample may contain only a few diseased cells (or nucleic acid derived from only a few diseased cells), particularly if the disease has not yet developed or spread to large portions of the body.

In some embodiments, small amounts of chimeric nucleic acid may be detected in a heterogeneous biological sample containing predominantly non-chimeric nucleic acids. For example, a sample may contain less than about 10%, less than about 5%, less than about 1%, less than about 0.1%, or less than about 0.01% chimeric nucleic acid relative to the amount of corresponding non-chimeric nucleic acid.

The selectivity provided by hybrid capture and amplification methods of the invention permit the detection of chimeric nucleic acids even from highly heterogeneous sources. Thus, methods of the invention are useful with a biopsy sample, despite contamination with blood cells and normal tissues, to detect a natural recombination associated with cancer or another disease state. Similarly, certain methods are useful with other patient samples, such as a body fluid sample (e.g., blood, serum, urine, sperm, vaginal secretions, prostatic secretions, nipple aspirate, lymph, saliva, tears, sweat, sputum, etc.), a fecal sample, or a tissue sample. Similarly, certain methods are useful to detect abnormal fetal nucleic acids in samples that also contain the corresponding normal maternal nucleic acids. Alternatively, samples from cultured eukaryotic or prokaryotic cells (e.g., a sample from a fermentation vat or from a flask of epithelial cells) or from other natural or artificial sources may be analyzed. Methods of the invention also are useful to detect an artificially-recombined nucleic acid (e.g., to monitor the integrity of a nucleic acid used in biopharmaceutical manufacture or to monitor a patient that received a therapeutic recombinant nucleic acid).

In some aspects of the invention, a sample may be interrogated for the presence of one or more specific chimeric nucleic acids (e.g., known translocation events) that are known to be associated with certain disease conditions. In other aspects, a sample may be interrogated for the presence of any chimeric nucleic acids wherein the presence of at least one chimeric nucleic acid (e.g., any translocation) may be indicative of genome instability associated with a disease such as adenoma or cancer, regardless of the identity of the chimeric nucleic acid.

In one aspect, methods of the invention include hybrid capturing a portion of the chimeric sequence that is not intended to be amplified, and then amplifying the portion of the chimera that was not used as a target for hybrid capture. For purposes of the invention, a chimeric sequence is one that contains a portion of a first nucleic acid (e.g., a portion of a first gene) and a portion of a second nucleic acid (e.g., a portion of a second gene) that are not normally (i.e., in a wild-type configuration) part of the same nucleic acid or not normally in proximity with each other. Thus, naturally-occurring chimeric sequences include nucleic acids from different chromosomes, as in a translocation, and include nucleic acids from a single chromosome brought into nonnatural proximity through a mutational event such as an inversion or a deletion.

According to one aspect of the invention, a chimeric nucleic acid may be amplified as shown in FIG. 1. The sample in FIG. 1 includes a first nucleic acid, a second nucleic acid, and a chimeric nucleic acid resulting from a recombination between the first and second nucleic acids. A capture probe is designed to hybridize with a portion of the first nucleic acid that is also present in the recombinant nucleic acid. This probe is used to capture any nucleic acid having its complement (i.e., a sequence with the first nucleic acid sequence). Any uncaptured nucleic acid is removed from the sample (or alternatively, captured nucleic acid is removed from the sample), thereby substantially isolating captured nucleic acid (which comprises the first nucleic acid and the chimeric nucleic acid that contains a portion of the first nucleic acid) from uncaptured nucleic acid (the second nucleic acid). Then, primers may be added to amplify the portion (e.g., a fragment thereof) of the second nucleic acid that is present in the chimeric nucleic acid. Any resulting amplicon from the reaction shown in FIG. 1 is determined to be from the chimeric nucleic acid since there is substantially no second nucleic acid to compete as a target. Furthermore, as shown in FIG. 1, amplicons may include nucleic acids corresponding exclusively to the portion of the second nucleic acid in the chimeric nucleic acid and may include nucleic acids also including a portion of the first nucleic acid present in the chimeric nucleic acid.

It is not essential to eliminate all of the wild-type second nucleic acid. If, after hybrid capture, the amount of chimeric nucleic acid exceeds the amount of the wild-type second nucleic acid, the wild-type second nucleic acid will not interfere substantially with amplification of the chimeric nucleic acid. Indeed, under those conditions, the chimeric nucleic acid will generally be the primary source of amplified nucleic acid. Thus, in one preferred embodiment, the amount of the chimeric nucleic acid exceeds the amount of the second nucleic acid (e.g., by at least 10%, at least 20%, at least 50%, at least 100%, or at least 200%) after capture and removal of substantially all of the second nucleic acid.

According to aspects of the invention, nucleic acids may be obtained from any source. In certain embodiments, nucleic acid may be isolated from stool (e.g., as described in Example 1). It should be appreciated that the amount of total nucleic acid that is isolated for analysis depends on the amount of biological sample that is processed. To detect rare events (e.g., events that are present at low frequencies because they are derived from small amounts of diseased cells or from small amounts of fetal cells) larger amounts of total nucleic acid should be analyzed. For example, stool samples of about 0.1-5 grams (e.g., 1-5 grams) may be analyzed. However, larger samples (e.g., greater than about 5 grams, 10 grams, 15 grams, 20 grams, 25 grams, 30 grams, 50 grams, or more)

may be processed to isolate total nucleic acid for subsequent analysis. In certain embodiments, a stool sample of 4.8 or 9.6 gram can be analyzed using the methods of the invention. Similarly, blood samples of any size may be analyzed. For example a blood sample of about 0.1-5 mls (e.g., 1-5 mls) may be analyzed. However, larger samples (e.g., greater than about 5 mls, 10 mls, 15 mls, 20 mls, 25 mls, 30 mls, 50 mls, or more) also may be analyzed. In certain embodiments, a biological sample may be processed to selectively isolate certain types of nucleic acid for subsequent analysis. For example, a stool sample may be processed to remove microbial nucleic acid and isolate total human nucleic acid (e.g., DNA) for subsequent analysis. However, in one embodiment, total nucleic acid from stool may be processed directly according to aspects of the invention to capture nucleic acids of interest (e.g., nucleic acids that hybridize to a capture probe that is complementary to a portion of the first nucleic acid of interest). Similarly, a blood sample may be processed to remove cells and isolate total free nucleic acid (e.g., DNA) for subsequent analysis. However, this step is not necessary.

Other types of samples may be used. For example other body fluids (e.g., sputum, urine, pus, cerebrospinal fluid, ejaculate, breast nipple aspirate, bile, etc.) or tissue biopsies may be used. Samples may be obtained from any subject, for example vertebrates, mammals (e.g., a cat, a dog, a horse, a cow, or a human). A human subject may be a patient that is being screened for the presence of a disease such as cancer. In one embodiment, the human patient may have one or more risk factors for cancer (e.g., hereditary, age, exposure to toxins or carcinogens, etc.). In one embodiment, a patient may be a cancer patient that is being monitored for disease progression, response to therapy or recurrence.

In one aspect, a nucleic acid sample may be fragmented using any appropriate method (e.g., sonication, enzymatic digestion, chemical degradation, etc.). In one embodiment, a fragmentation process may be used to obtain nucleic acid fragments of approximately the same size. However, fragmentation is not used when entire chromosomes are being analyzed. Also, the degree of fragmentation depends on the size of nucleic acid that is chosen for analysis. Aspects of the invention may be used to analyze any suitable nucleic acid fragment size that can be analyzed to detect a chimeric nucleic acid sequence. Fragments may range from 100 nucleotides in length to entire chromosomes, chromosome arms, or large fragments thereof. For example, fragments of about 1 kb, 10 kb, 100 kb, 1,000 kb, or more may be analyzed. The fragments may be single stranded or double stranded. A sample may contain a mixture of single and double stranded nucleic acids.

According to aspects of the invention, a capture step may be performed using any method known to those in the art. For example, nucleic acid capture may be performed using any suitable capture probe that hybridizes to a portion of a first nucleic acid (e.g., the probe may be complementary to a sequence of the first nucleic acid portion). However, it should be appreciated that in some embodiments a capture probe may be designed to hybridize to a junction region of a known, or suspected, chimeric event. For example, a capture probe may be complementary to a sequence that spans a junction between portions of two different chromosomes that have been joined due to a translocation. Similarly, a capture probe may be complementary to a junction between two portions that have been joined together due to a deletion or an inversion on one chromosome. It should be appreciated that more than one capture probe may be used to capture a nucleic acid of interest. For example, 2, 3, 4, 5, 10, or more different capture probes may be used. These capture probes may be complementary to different sequences of the nucleic acid portion that is being captured, or complementary to different nucleic acids being captured.

Capture probes may be DNA, RNA, PNA, or any suitable synthetic or modified nucleic acid, or any combination of two or more thereof. A capture probe may be immobilized on a bead, for example a streptavidin bead. In some embodiments, a capture probe is biotinylated. A bead may be at least 50 to 80 microns in diameter. However, other sizes (smaller or larger) also may be used. In other embodiments, a capture probe may be immobilized on a polyacrylamide gel (e.g., a gel which is associated with a membrane). One or more capture probes may be used. A capture probe can be of any suitable length that is adapted to capture a target molecule with sufficient specificity. A capture probe may be between 10 and 100 nucleotides in length (for example, at least 20, 25, 30, 35, 40, 50, 60, 70, 80, or 90 nucleotides in length). However, longer or intermediate length capture probes may be used. In certain embodiments, a capture probe is 37 nucleotides in length. In other embodiments, a capture probe is less than 100 nucleotides in length but at least 37 nucleotides in length. A capture probe is preferably single stranded. Capture probe(s) may be immobilized on a solid support and exposed to a nucleic acid sample in order to bind (and thereby capture) nucleic acid molecules containing a sequence that is complementary to the sequence of the capture probe(s). Unbound (non-complementary) nucleic acids may be removed using appropriate conditions (e.g., by washing the solid support using appropriate buffers, salt concentrations, and/or pH ranges, etc.).

According to aspects of the invention, a chimeric nucleic acid may be present in a low amount relative to corresponding non-chimeric nucleic acid (nucleic acid fragments containing the chimera between the first and second nucleic acids may be very rare relative to nucleic acid fragments that contain only the first or only the second nucleic acid). For example, the chimeric nucleic acid may represent less than about 10%, less than about 5%, less than about 1%, less than about 0.1%, or less than about 0.01% of the nucleic acid molecules that contain the captured sequence. Accordingly, a high efficiency capture method may be used to capture as much complementary nucleic acid as possible in order to maximize the probability of detecting a chimeric nucleic acid if it is present in the biological sample. In certain embodiments, the capture step is performed using repetitive reverse-field affinity electrophoresis (e.g., as described in Example 2).

According to aspects of the invention, any suitable assay may be used to detect the presence of a chimeric nucleic acid amongst the captured nucleic acid. For example, hybridization reactions (e.g., using labeled oligonucleotides, primer extension, molecular Beacons, etc.) may be used to detect the presence of a chimeric junction region amongst the captured nucleic acid. Alternatively, hybridization reactions may be used to detect the presence of a second nucleic acid amongst the captured first nucleic acid, wherein the first and second nucleic acids would not be expected to be present on the same nucleic acid molecule given the size of the captured nucleic acid fragments.

In certain embodiments, one or more amplification reactions (e.g., PCR, LCR, rolling circle, etc.) are used to assay for the presence of a chimeric nucleic acid. For each amplification reaction, one of the amplification primers is designed to hybridize to a sequence of the second nucleic acid that is not expected to be attached to the first nucleic acid on a normal (e.g., non-chimeric) molecule of the size that is captured. The second amplification primer may be designed to hybridize to a sequence on the first nucleic acid and any resulting amplification product would be a chimeric amplicon. Alternatively, the second amplification primer may be designed to hybridize to a sequence on the second nucleic acid and any resulting amplification product would be an amplicon derived entirely from a portion of the second nucleic acid. This amplicon would not be expected in the absence of a chimera, because the second nucleic acid is not captured in the absence of a chimeric nucleic acid. As discussed above, an amplification reaction may be designed to detect a predetermined chimeric event (e.g., a specific translocation). In one embodiment, an amplification reaction may include a primer that hybridizes to a specific chimeric junction region between first and second nucleic acids. However, in another aspect of the invention, the presence of any chimeric event may be sufficient to detect a disease. Accordingly, in some embodiments an assay may include two or more primer pairs designed to detect at least one of two or more different chimeric events. For example, a plurality of primer pairs (e.g., 2, 3, 4, 5, 6, 7, 8, 9, 10, 10-50, 50-100, or more) may be used to assay for the presence of at least one of many different chimeric events between any predetermined subset of different chromosomes (or all of the different chromosomes) and involving any predetermined group of different chromosomal regions.

According to the invention, amplification primers may be of any appropriate size (e.g., about 9-100 nucleotides long, for example about 15-80, about 30, or about 50 nucleotides long). Amplification primers may be DNA, RNA, PNA, or any suitable synthetic or modified nucleic acid, or any combination of two or more thereof. Amplification products may be detected using any appropriate methods (e.g., detectable labels, ethidium bromide staining, etc.). According to aspects of the invention, a control reaction may be used to determine whether the amount of detected chimeric nucleic acid (e.g., the amount of amplified product) is significant. In one embodiment, a control amount of amplification may be the amount of amplicon obtained in the absence of a chimeric nucleic acid. This amount may serve as a reference. The detection of an amplicon in an amount that is higher (e.g., significantly higher or statistically significantly higher) than the reference amount may be indicative of the presence of a chimeric nucleic acid in the captured nucleic acid sample.

In certain embodiments, amplification of a chimeric nucleic acid can be done selectively (i.e., such that the ratio of amplified product from the chimeric nucleic acid to amplified product from the wild-type second nucleic acid exceeds the pre-amplification ratio of chimeric nucleic acid to wild-type nucleic acid). For example, where amplification is done by PCR, one primer can hybridize, in whole or in part, to the portion of the first nucleic acid in the chimeric molecule, whereas the second primer hybridizes in whole or in part to the portion of the second nucleic acid in the chimeric molecule. Because only the chimeric molecule includes the first and second nucleic acids in proximity with each other, amplification is selective. Whereas the amount of chimeric nucleic acid preferably exceeds the amount of second nucleic acid when amplification is nonselective, much smaller amounts of chimeric nucleic acid are acceptable with selective amplification. Thus, after hybrid capture, the amount of chimeric nucleic acid can be relatively small (e.g., less than 10%, less than 1%, less than 0.1%, or less than 0.01% of the amount of the wild-type second nucleic acid), as only the chimeric nucleic acid should be amplified. Indeed, samples containing fewer than ten copies of the chimeric nucleic acid should be amenable to detection using methods of the invention. In certain embodiments, repetitive reverse-field electrophoresis may be used for a high yield capture of nucleic acids. This may be particularly useful for a sample suspected of containing a small total number and/or a small percentage of chimeric nucleic acid molecules relative to non-chimeric nucleic acid molecules.

According to aspects of the invention, a chimeric nucleic acid may result from any recombinant event (e.g., translocation, deletion, duplication, inversion, etc.) that results in two nucleic acids being associated on a single nucleic acid when they are normally on separate nucleic acids, or in two nucleic acids being brought closer together than normal on a single nucleic acid molecule. In a translocation event, the portions of the first and second nucleic acids may originate from different chromosomes. Under this circumstance, the capture probe is directed to a single chromosome and results in the capture of single chromosomes and chromosomes including a translocation event. The single chromosomes and translocated chromosomes can be separated using techniques such as PCR. A PCR reaction containing a first primer corresponding to a first chromosome and a second primer corresponding to a second chromosome will not detect the single chromosome and will only detect the translocated chromosomes in the sample. It should be appreciated that capture probes and amplification probes may be designed to hybridize to any regions of first and second nucleic acids and will be useful to detect chimeric nucleic acids that contain both the first and second nucleic acid regions if the size of the captured nucleic acid is sufficient to contain both regions of the chimera. Accordingly, aspects of the invention may be used to design assays to detect the presence of one or more different types of translocations in a biological sample (e.g., a reciprocal translocation, a Robertsonian translocation, a balanced translocation, and/or an unbalanced translocation) involving any predetermined combination of chromosomes or chromosome regions.

As indicated above, the chimeric nucleic acid to be detected can be the result of, for example, an inversion, deletion or translocation event. In inversions and deletions, the portions of the first and second nucleic acids that are placed in proximity with each other by the mutational event originate from the same chromosome. Thus, if the chromosome is intact, a capture probe that hybridizes to the chimeric nucleic acid and to the first nucleic acid will also capture the second nucleic acid because it is attached to the first nucleic acid. Under those circumstances, hybrid capture would fail to purify the chimeric nucleic acid from the second nucleic acid. Accordingly, when performing hybrid capture for an inversion or deletion, the wild-type chromosome is preferably not intact, but is shorn or cleaved (e.g. enzymatically) to separate the first and second nucleic acids on the wild-type chromosome, facilitating purification. In aspects of the invention, one or more fragments of a chromosome are captured. A chromosome fragment can be at least 1 kb, 5 kb, 10 kb, 25 kb, 50 kb, or 100 kb. However, smaller, larger, or intermediate fragment sizes may be used.

According to aspects of the invention, the presence of one or more chimeric nucleic acid molecules in a biological sample may be indicative of one or more conditions in the subject that the sample was obtained from. Accordingly, aspects of the invention may be used to detect one or more indicia of a disease or condition such as cancer, adenoma, a tumor or other disease or condition associated with a chimeric nucleic acid. Aspects of the invention also may be used to detect one or more chimeric events indicative of fetal chromosomal abnormalities. For example, the presence of a translocation involving chromosome 21 may be indicative of an unbalanced translocation associated with Down's syndrome). Aspects of the invention also may be used to detect the presence of microbial infections such as bacterial or viral infections (e.g., certain microbes such as retroviruses may integrate into chromosomal loci thereby creating chimeric nucleic acid sequences). In one embodiment, aspects of the invention may be used to detect rare cells that are infected with a microbe such as a virus (e.g, an HIV virus). In one embodiment, aspects of the invention may be used to monitor the progress of a treatment or recurrence or progression of an infection by monitoring the number of cells that are infected by a microbe such as a virus (e.g., an HIV virus).

In practice, methods of the invention are useful on any type of nucleic acid. When methods are used with RNA, it is preferable to isolate total RNA using, for example, a poly-A capture scheme. A cDNA is then made from the collective RNA either before or after hybrid capture of the chimeric nucleic acids and selective amplification. Any known amplification method is useful in the invention as is any known capture method, as the selection of techniques does not affect the operation of the invention as described herein. It should be appreciated that capture/amplification primers may contain one or a few non-complementary nucleotides (e.g., at the tails) in addition to the complementary sequences.

EXAMPLES

Example 1

Isolation of Chimeric Nucleic Acid

A stool sample is collected and suspended in any appropriate buffer (e.g., Tris-HCl containing EDTA). DNA is isolated from the stool sample, biotinylated, and SDS is added and the sample is denatured by heat. The sample is applied to the electrophoretic medium in an electrophoresis tank. The DNA is passed over a capture cartridge containing one or more biotinylated DNA capture probes immobilized on streptavidin beads (Ultralink® Immobilized streptavidin beads, Pierce, Rockford, Ill.) using electric current at 200 mA for 90 minutes. The electric current is reversed and the DNA is passed over the capture cartridge in the opposite direction using electric current at 200 mA for 90 minutes. The process is repeated for 15 cycles. The capture cartridge is removed from the electrophoresis tank and placed onto a microtitre plate. Buffer is applied to the capture cartridge and the beads are centrifuged. The capture cartridge is transferred to another plate and 100 µl of NaOH (0.1N) is applied to the beads and incubated for 30 minutes. The captured DNA is collected by centrifugation and neutralized with neutralization buffer.

The isolated DNA is amplified using PCR containing primers corresponding to the area adjacent to the translocation. For example, a first primer corresponds to the adjacent region of one chromosome indicated in the translocation event and a second primer corresponds to the adjacent region of a second chromosome indicated in the translocation event. A positive result, e.g. a band on a polyacrylamide gel, indicates the presence of that particular chromosome translocation.

Example 2

Figure 2:
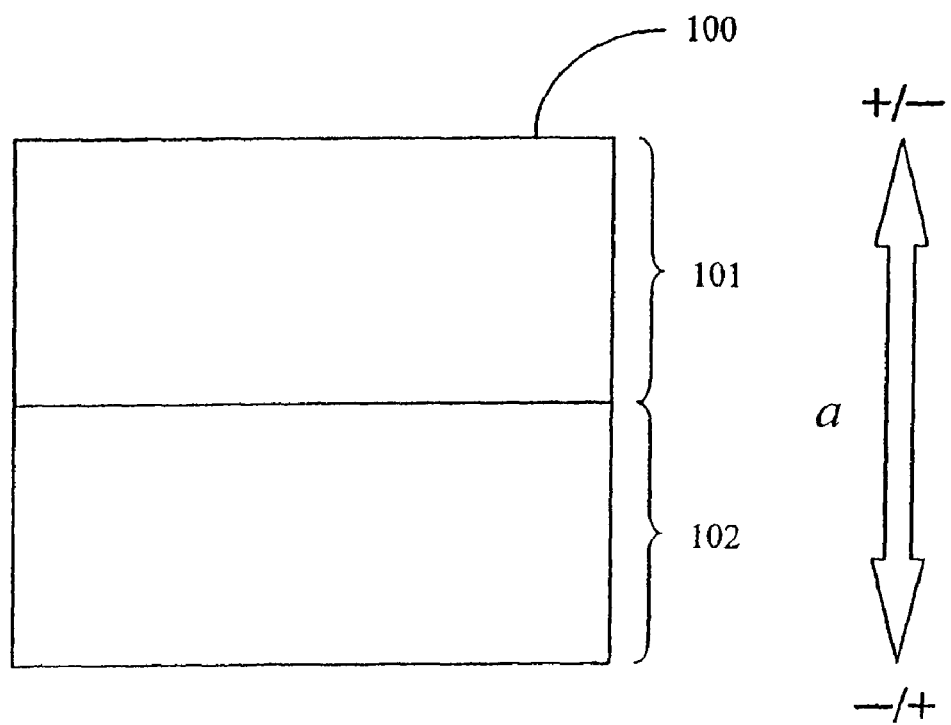
FIG. 2. Schematic diagram of an electrophoretic device having an electrophoretic medium (100) with two regions, a first region 101 and a second region 102.

In certain embodiments, a nucleic acid sample is subjected to repetitive reversed-field affinity electrophoresis in an electrophoretic medium having at least one capture region comprising an electrophoretic medium with a bound capture probe. In one embodiment, the electrophoretic medium has at least two regions arranged consecutively, e.g., in a first spatial dimension (see FIG. 2, for example). At least one of the regions includes a first nucleic acid (e.g., DNA, RNA, PNA, synthetic nucleic acid or combination thereof) capture probe capable of capturing a chimeric nucleic acid molecule. The electrophoretic medium is first subjected to an electric field in a first direction resulting in migration within the medium of charged molecules amongst the regions in the first spatial dimension. The electric field is then reversed such that the electrophoretic medium is subjected to an electric field in a second direction substantially antiparallel to the first direction, resulting in migration within the medium of charged molecules in the test sample amongst the regions in the first spatial dimension. This process of reversing the electric field and electrophoresing the sample in the opposite direction can be repeated one or more times. For example, the sample can be subjected to 5, 10, 20, 30 or more cycles of reversed-field electrophoresis in which the sample is electrophoresed in one direction and then the opposite direction. In an embodiment, the first and second electrophoretic fields comprise between about 1 mAmp to about 200 mAmps, depending upon the electrophoretic medium used (e.g., concentration of agarose or polyacrylamide, pH, temperature) and size of the molecule or cell being separated or isolated. In another embodiment, the first and second electrophoretic fields cause the chimeric nucleic acid sample to move through the medium at a rate of between about 1 mm/min to about 100 cm/min. However, any suitable rate may be used (e.g., any suitable current may be used). In a further embodiment, each of the electrophoretic fields is run for any appropriate time. The length of each cycle can be 5, 10, 15, 20, 25, 30, 35, 40, 45, 50, 55, 60, 65, 70, 75, 80, 85, 90, 95, 100, 105, 110, 115, or 120 minutes. In one embodiment, each cycle of electrophoresis is run for a period of at least 90 minutes. However, any suitable period for each cycle may be used. The number of cycles can be about or at least 2, 3, 4, 5, 6, 7, 8, 9, 10, 15, 20, 25, 30, 35, 40, 45, 50, 100, etc. However, any suitable number of cycles may be used.

In some embodiments, the medium has a multiplicity of regions arranged consecutively in the first spatial dimension, and each such region includes nucleic acid capture probes capable of capturing different chimeric nucleic acid molecules. In these embodiments, a multiplicity of different nucleic acid capture probes are selectively bound to the multiplicity of chimeric nucleic acid molecules in a sample. In certain embodiments, there are 5-10, 5-50, 5-100 or more different regions including different nucleic acid capture probes.

Appropriate conditions for electrophoresis, including buffer systems, temperature, and voltage, can be chosen by those of skill in the art, according to well known principles, depending upon the type of sample and chimeric nucleic acid molecules being assayed and the type of electrophoretic medium being employed. For example, because the chimeric nucleic acid molecules must be charged in order to migrate in an electric field, buffers of suitable pH are chosen such that the chimeric nucleic acid molecules are appropriately charged during electrophoresis. In some embodiments, the buffers can be varied during or between electrophoretic steps or cycles in order to alter the charges of the chimeric nucleic acid molecules and thereby affect electrophoretic separation. In addition, buffers can be chosen which promote greater or lesser degrees of stringency or selectivity of capture by the nucleic acid capture probes.

Electrophoretic media useful in the invention include any media through which charged molecules can migrate in solution in response to an electric field and to which nucleic acid capture probes can be immobilized, including polymeric matrices of gels, packed volumes of particles or beads, and hybrid media including beads or particles embedded in a polymeric gel matrix.

In some embodiments, one or more regions of the electrophoretic medium can be formed from different materials than the other regions (e.g., different polymeric matrices, different packed beads, hybrid gel-bead media, and combinations thereof). The materials for the different regions can be selected according to principles well known in the art.

In some embodiments, one or more of the regions of the electrophoretic medium are formed as a polymeric gel. Commonly used gel media useful in the invention include polymeric gels formed from monomers of acrylamide, agarose, starches, dextrans, and celluloses, as well as chemically modified or functionalized variants of these monomers (see, e.g., Polysciences, Inc., Polymer & Monomer catalog, 1996-1997, Warrington, Pa.), (Smithies (1959), *Biochem. J* 71:585; Quesada (1997), *Curr. Opin. Biotech.* 8:82-93).

In other embodiments, packed volumes of small beads or particle beds can be used as electrophoretic media. Such particle beds, which are frequently used in chromatography, have the advantage of large interstitial voids which allow for the passage of large molecules such as nucleic acid fragments >1 kb. In some embodiments, the beads have average diameters in the range of 1-5 µm, 5-50 µm, or 50-150 µm, although larger beads can also be used. Beads useful in the invention can be formed from materials including, but not limited to, agarose polymers, dextran polymers, acrylic polymers, glass, latex, polystyrene, poly(hydroxyethylcellulose), poly(ethylenoxide), a modified acrylamide, acrylate ester, cellulose, or carbohydrates etc.

Beads useful in the invention can be solid beads or porous beads, In some embodiments, porous beads will have diameters in the range of 10-20 µm or, more generally 10-50 µm, and can have a wide range of pore sizes. Such porous beads can include nucleic acid capture probes embedded within the pores and/or bound to the surfaces of the probes. Non-porous or solid beads can have a wider range of diameters, including without limitation beads in the range of 1-100 µm.

Such beads conveniently can be coated (including the interiors of pores) with one member of a nucleic acid capture probe pair such that nucleic acid capture probes bound to the other member of the nucleic acid capture probe pair can be immobilized on the beads. For example, and without limitation, beads can be coated with avidin or streptavidin and nucleic acid capture probes can be conjugated to biotin to cause immobilization of the nucleic acid capture probes on the beads. Similarly, probes can be coated with Protein A to immobilize antibody nucleic acid capture probes that bind to Protein A. Beads also can be treated or coated to reduce non-specific binding of other molecules in a sample. For example, beads can be treated to reduce the number of hydrophobic groups (e.g., benzyl groups) on the surface, or to increase the number of hydrophilic groups (e.g., carboxyl groups) on the surface. Beads can also be coated with gelatin, bovine serum albumin or other molecules that will non-specifically bind to and "block" the surface prior to use with a sample.

In embodiments employing beads as electrophoretic media, it may be necessary to separate different regions of the electrophoretic medium by separators which are membranes or meshes that prevent the movement of the beads from one region to another in response to the electric field. Such separators must have pores sufficiently large to be permeable to the nucleic acid capture probes, but not permeable to the beads. Such separators can be used alone, or in combination with spacer elements or other structures between regions of the electrophoretic medium.

The electrophoretic medium can be maintained at a chosen temperature to prevent denaturation of biomolecules (e.g., <37° C.) or to promote denaturation (e.g., 60° C.-90° C). In some embodiments, the temperature can be varied during or between electrophoretic steps or cycles in order to alter the binding of the chimeric nucleic acid molecules and thereby affect electrophoretic separation.

Similarly, the electric field across an electrophoretic medium can be chosen according to principles well known in the art. In particular, voltages are chosen which cause a current which allows the chimeric nucleic acid molecules to migrate amongst regions in a reasonable period of time without causing substantial temperature increases in the medium which might disrupt either the chimeric nucleic acid molecules or the medium itself. Typically, for protein electrophoresis in an SDS-polyacrylamide gel, currents of 2-20 mA can be used, whereas for agarose gel electrophoresis of nucleic acids, a current of 100-200 mA can be used. These and other aspects of repetitive reversed-field electrophoresis are described in U.S. application Ser. No. 10/982,733, filed Nov. 5, 2004, published as US 2005-0247563 A1, and PCT application Ser. No. PCT/US2004/0036904, filed Nov. 5, 2004, published on May 26, 2005 as WO2005/047881, the technical details of both of which are herein incorporated in their entirety by reference.

In aspects of the invention, a sample may be added directly to the electrophoretic medium. In other aspects, a sample is pre-treated before addition to the electrophoretic medium. In some embodiments, a sample is prepared according to standard sample preparation techniques, optionally including partial purification, which render the chimeric nucleic acid molecules more accessible to binding partners during electrophoresis. For example, and without limitation, blood samples can be centrifuged to separate fractions including whole cells or membranes from serum, feces samples can be sectioned and homogenized with physiologically acceptable buffer and detergent (see, e.g., U.S. Pat. Nos. 5,741,650, 6,503,718), and sputum samples can be liquefied and fractionated. Antibiotics or bactericides optionally can be added to samples to prevent further growth of any organisms present. Sodium dodecyl sulfate (SDS) can be added to samples and denatured using heat as standard in the art. Whole cells can be removed or can be lysed to release their contents. For assays in which nucleic acids are to be detected, proteinases and inhibitors of DNA and RNA degrading enzymes optionally can be added. In addition, nucleic acids optionally can be amplified prior to detection.

Example 3

Methods of the invention are useful for detecting chromosome translocation events associated with diseases or conditions. Accordingly, aspects of the invention may be used to detect one or more of the following deletions, translocations, and provide indicia of one or more of the following diseases or conditions. Diseases or conditions associated with rearrangements (e.g., translocations, deletions, etc.) involving different chromosomes include cancers, tumors, fetal abnormalities, developmental abnormalities, etc. For example, leukaemia has been associated with at least the following chromosomal rearrangements involving chromosome X: t(X;10) (p10;p10); t(X;11)(q13;q23); t(X;2)(q11;p23); t(X;20)(q13; q13.3); t(X;21)(p22;q22); t(X;6)(p11;q23). Similarly, solid tumors have been associated with at least the following chromosomal rearrangements involving chromosome X: t(X;1) (p11.2;p34) in renal cell carcinoma; t(X;1)(p11.2;q21.2) in renal cell carcinoma; Primary renal ASPSCR1-TFE3 t(X;17) (p11;q25) tumor; t(X;17)(p11.2;q23) in renal cell carcinoma; t(X;17)(p11;q25); t(X;18)(p11.2;q11.2). Similarly, leukaemia has been associated with at least the following chromosomal rearrangements involving chromosome y; t(Y;1)(q12;q12).

Leukemia has been associated with at least the following chromosomal rearrangements involving chromosome 1: t(1;11)(q21;q23); t(1;12)(p36;p13); t(1;12)(q25;p13); t(1;13)(q32;q14); t(1;14)(p22;q32) in non Hodgkin's lymphoma (NHL); t(1;14)(p32;q11); t(1;14)(q21;q32) BCL9/IGH; t(1;14)(q21;q32) FCGR2B/IGH; t(1;14)(q21;q32) IRTA1/IGH; t(1;14)(q21;q32) MUC1/IGH; t(1;14)(q25;q32); t(1;16)(q11;q11); t(1;16)(q12;q24); t(1;18)(q10;q10); t(1;18)(q25;q23); t(1;19)(p13;p13.1); t(1;19)(q23;p13); t(1;2)(q12;q37); t(1;2)(q25;p23); t(1;21)(p32;q22); t(1;21)(p36;q22); t(1;22)(p13;q13); t(1;22)(q21;q11); t(1;3)(p32;p21); t(1;3)(p36;p21); t(1;3)(p36;q21); t(1;5)(p32;q31); t(1;6)(p35;p25); t(1;7)(p32;q34); t(1;7)(p34;q34); t(1;7)(p36;q34); t(1;7)(q10;p10); t(1;7)(q21;q22); t(Y;1)(q12;q12). Similarly, solid tumors have been associated with at least the following chromosomal rearrangements involving chromosome 1: t(X;1)(p11.2;q21.2) in renal cell carcinoma; t(1;2)(q25;p23); t(1;13)(p36;q14); t(1;17)(p34;p13); t(1;2)(q25;p23); t(1;3)(p36;.3q25); t(1;3)(q22;q12).

Leukemia has been associated with at least the following chromosomal rearrangements involving chromosome 2: t(1;2)(q12;q37); t(1;2)(q25;p23); t(2;11)(p21;q23); t(2;14)(p13;q32); t(2;17)(p23;q23); t(2;17)(p23;q25); t(2;18)(p11;q21); t(2;21)(p11;q22); t(2;22)(p23;q11.2); t(2;3)(p12;q27); t(2;3)(p15-23;q26-27); t(2;3)(p15-p23;q26-27); t(2;3)(p23;q21); t(2;4)(p23;q25-q35); t(2;5)(p23;q35); t(2;8)(p12;q24); t(X;2)(q11;p23). Similarly, solid tumors have been associated with at least the following chromosomal rearrangements involving chromosome 2: t(1;2)(q25;p23); t(2;2)(p23;q13); t(2;11)(p23;p15); t(2;17)(p23;q23); t(2;19)(p23;p13.1); t(1;2)(q25;p23); t(2;11)(p23;p15); t(2;13)(q35;q14); t(2;17)(p23;q23); t(2;19)(p23;p13.1); t(2;2)(p23;q13); t(2;22)(q23;q12).

Leukemia has been associated with at least the following chromosomal rearrangements involving chromosome 3: t(1;3)(p32;p21); t(1;3)(p36;p21); t(1;3)(p36;q21); t(2;3)(p12;q27); t(2;3)(p15-23;q26-27); t(2;3)(p15-p23;q26-27); t(2;3)(p23;q21); t(3;11)(p21;q23); t(3;11)(q25;q23); t(3;11)(q28;q23); t(3;12)(q26;p13); t(3;13)(q27;q14); t(3;14)(p14;q32); t(3;14)(q21;q32); t(3;14)(q27;q32); t(3;21)(q26;q22) in treatment related leukemia; t(3;21)(q26;q22); t(3;22)(q27;q11); t(3;3)(q21;q26); t(3;4)(q27;p13); t(3;5)(q25;q34); t(3;Var)(q27;Var) in non Hodgkin lymphoma. Similarly, solid tumors have been associated with at least the following chromosomal rearrangements involving chromosome 3: t(1;3)(p36;.3q25); t(1;3)(q22;q12); t(3;12)(q27;q15); t(3;12)(q28;q15); t(3;17)(q21;p13).

Leukemia has been associated with at least the following chromosomal rearrangements involving chromosome 4: t(2;4)(p23;q25-q35); t(3;4)(q27;p13); t(4;11)(q21;p15); t(4;11)(q21;q23); t(4;12)(p16;p13); t(4;12)(q11-q21;p13); t(4;14)(p16;q32); t(4;21)(q31;q22); t(4;22)(q12;q11.2).

Leukemia has been associated with at least the following chromosomal rearrangements involving chromosome 5: t(1;5)(p32;q31); t(2;5)(p23;q3 5); t(3;5)(q25;q34); t(5;10)(q33;q21); t(5;11)(q31;q23); t(5;11)(q35;p15.5); t(5;12)(q33;p13); t(5;14)(q31;q32); t(5;14)(q33;q24).; t(5;14)(q33;q32); t(5;14)(q35;q32); t(5;15)(15;q11-13); t(5;17)(q13;q21); t(5;17)(q33;p11.2); t(5;17)(q35;q21); t(5;21)(q13;q22); t(5;7)(q33;q11).

Leukemia has been associated with at least the following chromosomal rearrangements involving chromosome 6: t(1;6)(p35;p25); t(6;11)(q27;q23); t(6;14)(p21;q32); t(6;21)(p22;q22); t(6;8)(q11;q11); t(6;8)(q27;p12); t(6;9)(p23;q34); t(X;6)(p11;q23). Similarly, solid tumors have been associated with at least the following chromosomal rearrangements involving chromosome 6: t(6;1)(p21;q12) in renal cell carcinoma.

Leukemia has been associated with at least the following chromosomal rearrangements involving chromosome 7: t(1;14)(p32;q11); t(1;7)(p32;q34); t(1;7)(p34;q34); t(1;7)(p36;q34); t(1;7)(q10;p10); t(1;7)(q21;q22); t(5;7)(q33;q11); t(7;10)(q34;q24); t(7;1)(p15;p15); t(7;11 )(q35;p13); t(7;12)(p12;q13); t(7;12)(q36;p13); t(7;14)(q22;q1_); t(7;19)(q34;p13); t(7;9)(q34;q32); t(7;9)(q34;q34). Similarly, solid tumors have been associated with at least the following chromosomal rearrangements involving chromosome 7: Pericytoma with t(7;12); t(7;22)(p22;q12); t(7;8)(p22;q12); t(7;8)(q31;q13).

Leukemia has been associated with at least the following chromosomal rearrangements involving chromosome 8: t(2;8)(p12;q24); t(6;8)(q11;q11); t(6;8)(q27;p12); t(8;11)(p11;p15); t(8;12)(q22;q13); t(8;13)(p12;q12); t(8;14) (q24;q11); t(8;14)(q11;q32); t(8;14)(q24;q32); t(8;16)(p11;p13) in treatment related leukemia; t(8;16)(p11;p13); t(8;19) (p11;q13); t(8;21)(q22;q22) in treatment related leukemia; t(8;21)(q22;q22); t(8;21)(q24;q22); t(8;22) (p11;q13); t(8;22)(p11;q11); t(8;22)(q24;q11); t(8;9)(p12;q33). Similarly, solid tumors have been associated with at least the following chromosomal rearrangements involving chromosome 8: t(7;8)(p22;q12).

Leukemia has been associated with at least the following chromosomal rearrangements involving chromosome 9: t(6;9)(p23;q34); t(7;9)(q34;q32); t(7;9)(q34;q34); t(8;9)(p12;q33); t(9;11)(p22;q23); t(9;11)(q34;p15); t(9;11)(q34;q23); t(9;12)(p24;p13); t(9;12)(q22;p12); t(9;12)(q34;p13); t(9;14)(p13;q32); t(9;14)(q34;q32); t(9;22)(q34;q11) in ALL; t(9;22)(q34;q11) in ANLL; t(9;22)(q34;q11) in CML; t(9;22)(q34;q11) in treatment related leukemia. Similarly, solid tumors have been associated with at least the following chromosomal rearrangements involving chromosome 9: t(9;15)(q22;q21); t(9;17)(q22;p13); t(9;17)(q22;q11); t(9;22)(q22;q12).

Leukemia has been associated with at least the following chromosomal rearrangements involving chromosome 10: t(10;11)(p1.2;q23); t(10;11)(p12;q23); t(10;11)(p13;q21); t(10;11)(q25;p15); t(10;14)(q24;q11); t(5;10)(q33;q21); t(7;10)(q34;q24); t(X;10)(p10;p10). Leukemia has been associated with at least the following chromosomal rearrangements involving chromosome 11: t(10;11)(p11.2;q23); t(10;11)(p12;q23); t(10;11)(p13;q21); t(10;11)(q25;p15); t(11;12)(p15;q13); t(11;12)(q23;q13) (/HMGA2); t(11;12)(q23;q13) (MLL/CIP29); t(11;14)(p11;q32); t(11;14)(p13;q11); t(11;14)(p15;q11); t(11;14)(q13;q32) in multiple myeloma; t(11;14)(q13;q32); t(11;14)(q23;q24); t(11;15)(q23;q14); t(11;16)(q23;p13); t(11;17)(q13;q21); t(11;17)(q23;p13); t(11;17)(q23;q12); t(11;17)(q23;q21); t(11;17)(q23;q25); t(11;18)(q21;q21); t(11;19)(q23;p13.1); t(11;19)(q23;p13.3); t(11;20)(p15;q11); t(11;22)(q23;q11.2); t(11;22)(q23;q13); t(1;11)(q21;q23); t(2;11)(p21;q23); t(3;11)(p21;q23); t(4;11)(q21;p15); t(4;11)(q21;q23); t(5;11)(q31;q23); t(5;11)(q35;p15.5); t(6;11)(q27;q23); t(7;1)(p15;p 15); t(7;11)(q35;p13); t(8;11)(p11;p15); t(9;11)(p22;q23); t(9;11)(q34;p15); t(9;11)(q34;q23); t(X;11)(q13;q23). Similarly, solid tumors have been associated with at least the following chromosomal rearrangements involving chromosome 11: t(6;11)(p21;q12) in renal cell carcinoma; t(2;11)(p23;p15); t(11;16)(q13;p13); t(11;22)(p13;q12); t(11;22)(q24;q12); t(2;11)(p23;p15).

Leukemia has been associated with at least the following chromosomal rearrangements involving chromosome 12: t(11;12)(q23;q13) (/HMGA2); t(1;12)(q23;q13) (MLL/

CIP29); t(12;12)(p13;q13); t(12;13)(p12;q12-14); t(12;14) (q13;q31); t(12;20)(q15;q11.2); t(12;21)(p12;q22); t(12;21) (q24;q22); t(12;22)(p13;q11-12); t(1;12)(p36;p13); t(1;12) (q25;p13); t(3;12)(q26;p13); t(4;12)(p16;p13); t(4;12)(q11-q21;p13); t(5;12)(q33;q13); t(7;12)(p12;q13); t(7;12)(q36; p13); t(8;12)(q22;q13); t(9;12)(p24;p13); t(9;12)(q22;p12); t(9;12)(q34;p13). Similarly, solid tumors have been associated with at least the following chromosomal rearrangements involving chromosome 12: Pericytoma with t(7;12); t(11;16) (q13;p13); t(11;22)(q24;q12); t(12;15)(p13;q26); t(12;16) (q13;p11); t(3;12)(q27;q15); t(3;12)(q28;q15).

Leukemia has been associated with at least the following chromosomal rearrangements involving chromosome 13: t(12;13)(p12;q12-14); t(1;13)(q32;q14); t(3;13)(q27;q14); t(8;13)(p12;q12). Similarly, solid tumors have been associated with at least the following chromosomal rearrangements involving chromosome 13: t(11;16)(q13;p13); t(1;13)(p36; q14); t(2;13)(q35;q14).

Leukemia has been associated with at least the following chromosomal rearrangements involving chromosome 14: t(10;14)(q24;q11); t(11;14)(p11;q32); t(11;14)(p13;q11); t(11;14)(p15;q11); t(11;14)(q13;q32) in multiple myeloma; t(11;14)(q13;q32); t(11;14)(q23;q24); t(12;14)(q13;q31); t(14;21)(q11;q22); t(14;14)(q11;q32.1); t(14;18)(q32;q21); t(14;19)(q32;q13) in acute lymphoblastic leukaemia; t(14; 19)(q32;q13); t(14;21)(q22;q22); t(1;14)(p22;q32) in non Hodgkin's lymphoma (NHL); t(1;14)(q21;q32) BCL9/IGH; t(1;14)(q21;q32) IRTA1/IGH; t(1;14)(q21;q32) MUC1/IGH; t(1;14)(q25;q32); t(2;14)(p3;q32); t(3;14)(p14;q32); t(3;14) (q21;q32); t(3;14)(q27;q32); t(4;14)(p16;q32); t(5;14)(q31; q32); t(5;14)(q33;q24); t(5;14)(q33;q32); t(5;14)(q35;q32); t(6;14)(p21;q32); t(7;14)(q22;q1_); t(8;14) (q24;q11); t(8; 14)(q11;q32); t(8;14)(q24;q32); t(9;14)(p13;q32); t(9;14) (q34;q32).

Leukemia has been associated with at least the following chromosomal rearrangements involving chromosome 15: t(11;15)(q23;q14); t(15;17)(q22;q21) in treatment related leukemia; t(15;17)(q22;q21); t(15;21)(q22;q22); t(5;15) (p15;q11-13). Similarly, solid tumors have been associated with at least the following chromosomal rearrangements involving chromosome 15: t(11;22)(q24;q12); t(9;15)(q22; q21); t(9;17)(q22;q11).

Leukemia has been associated with at least the following chromosomal rearrangements involving chromosome 16: t(11;16)(q23;p13); t(16;16)(p13;q22); t(16;21)(q24;q22); t(1;16)(q11;q11); t(1;16)(q12;q24); t(8;16)(p11;p13) in treatment related leukemia; t(8;16)(p11;p13). Similarly, solid tumors have been associated with at least the following chromosomal rearrangements involving chromosome 16: t(11; 16)(q13;p13); t(12;15)(p13;q26); t(12;16)(q13;p11); t(16; 17)(q22;p13).

Leukemia has been associated with at least the following chromosomal rearrangements involving chromosome 17: t(11;17)(q13;q21); t(11;17)(q23;p13); t(11;17)(q23;q12); t(11;17)(q23;q21); t(11;17)(q23;q25); t(15;17)(q22;q21) in treatment related leukemia; t(15;17)(q22;q21); t(17;19)(q22; p13); t(17;21)(q11.2;q22); t(2;17)(p23;q23); t(2;17)(p23; q25); t(5;17)(q13;q21); t(5;17)(q33;p11.2); t(5;17)(q35;q2 1). Similarly, solid tumors have been associated with at least the following chromosomal rearrangements involving chromosome 17: Primary renal ASPSCR1-TFE3 t(X;17)(p11; q25) tumor; t(X;17)(p11.2;q23) in renal cell carcinoma; t(2; 17)(p23;q23); t(12;22)(q13;q12); t(16;17)(q22;p13); t(1;17) (p34;p13); t(2;17)(p23;q23); t(3;17)(q21;p13); t(9;17)(q22; p13); t(9;17)(q22;q11); t(X;17)(p11;q25).

Leukemia has been associated with at least the following chromosomal rearrangements involving chromosome 18: t(1; 18)(q21;q21); t(14;18)(q32;q21); t(18;21)(q21;q22); t(18; 22)(q21;q11); t(1;18)(q10;q10); t(1;18)(q25;q23); t(2;18) (p1;q21). Similarly, solid tumors have been associated with at least the following chromosomal rearrangements involving chromosome 18: t(X;18)(p11.2;q11.2).

Leukemia has been associated with at least the following chromosomal rearrangements involving chromosome 19: t(1; 19)(q23;p13.1); t(11;19)(q23;p13.3); t(14;19)(q32;q13) in acute lymphoblastic leukaemia; t(14;19)(q32;q13); t(17;19) (q22;p13); t(19;21)(q13.4;q22); t(1;19)(p13;p13.1); t(1;19) (q23;p13); t(7;19)(q34;p13); t(8;19) (p11;q13). Similarly, solid tumors have been associated with at least the following chromosomal rearrangements involving chromosome 19: t(2; 19)(p23;p13.1); t(2;19)(p23;p13.1).

Leukemia has been associated with at least the following chromosomal rearrangements involving chromosome 20: t(11;20)(p15;q11); t(12;20)(q15;q11.2).; t(20;21)(q13;q22); t(X;20)(q13;q13.3).

Leukemia has been associated with at least the following chromosomal rearrangements involving chromosome 21: t(12;21)(p12;q22); t(12;21)(q24;q22); t(14;21)(q11;q22); t(14;21)(q22;q22); t(15;21)(q22;q22); t(16;21)(p11;q22); t(16;21)(q24;q22); t(17;21)(q11.2;q22); t(18;21)(q21;q22); t(19;21)(q13.4;q22); t(1;21)(p32;q22); t(1;21)(p36;q22); t(20;21)(q13;q22); t(2;21)(p11;q22); t(3;21)(q26;q22) in treatment related leukemia; t(3;21)(q26;q22); t(4;21)(q31; q22); t(5;21)(q13;q22); t(6;21)(p22;q22); t(8;21)(q22;q22) in treatment related leukemia; t(8;21)(q22;q22); t(8;21)(q24; q22); t(X;21)(p22;q22). Similarly, solid tumors have been associated with at least the following chromosomal rearrangements involving chromosome 21: t(16;21)(p11;q22); t(17;22)(q12;q12).

Leukemia has been associated with at least the following chromosomal rearrangements involving chromosome 22: t(11;22)(q23;q11.2); t(11;22)(q23;q13); t(12;22)(p13;q11-12); t(18;22)(q2;q11); t(1;22)(p13;q13); t(1;22)(q2;q11); t(2; 22)(p23;q11.2); t(3;22)(q27;q11); t(4;22)(q12;q11.2); t(8;22) (p11;q13); t(8;22)(p11;q11); t(8;22)(q24;q11); t(9; 22)(q34;q11) in ALL; t(9;22)(q34;q11) in ANLL; t(9;22) (q34;q11) in CML; t(9;22)(q34;q11) in treatment related leukemia. Similarly, solid tumors have been associated with at least the following chromosomal rearrangements involving chromosome 22: t(11;22)(p13;q12); t(11;22)(q24;q12); t(12; 16)(q13;p11); t(12;22)(q13;q12); t(17;22)(q12;q12); t(17; 22)(q22;q13); t(21;22)(q22;q12); t(2;22)(q23;q12); t(7;22) (p22;q12); t(9;22)(q22;q12).

Aspects of the invention may be used to detect chimeric nucleic acid molecule(s) involving one or more translocations, deletions, inversions, insertions or other recombination events involving one or more disease-associated nucleic acids or genes (e.g., tumor suppressor(s), oncogene(s), mismatch repair, kinase, phosphatase, or receptor gene(s), etc.).

In other aspects, methods of the invention may be used to detect fetal indicia of rare disorders caused by minor chromosomal changes. For example, a small deletion on chromosome 15 associated with Prader-Willi syndrome may be detected. Similarly, a small deletion on chromosome 5 associated with cri-du-chat (cat cry) syndrome, and small deletions from a specific section of chromosome 22 associated with heart defects, cleft palate and other problems seen in DiGeorge and velocardiofacial syndromes also may be detected.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

I claim:

1. A method for detecting a chromosome translocation event in a DNA sample comprising
adding a DNA sample to an immobilized DNA capture probe capable of hybridizing to said DNA sample, wherein said DNA sample is repeatedly exposed to the immobilized DNA capture probe using reverse-field electrophoresis;
removing the captured DNA sample from the DNA capture probe and amplifying the captured DNA sample.

2. The method of claim 1, wherein the DNA capture probe is immobilized on one or more beads.

3. The method of claim 1, wherein two or more DNA capture probes are immobilized on a gel associated with a membrane.

4. The method of claim 1, wherein two or more DNA capture probes are immobilized.

5. The method of claim 1, wherein the captured DNA sample is amplified using a PCR reaction.

6. The method of claim 5, wherein a first primer and a second primer are present in the PCR reaction.

7. The method of claim 6, wherein the first primer corresponds to a region of a first chromosome.

8. The method of claim 6, wherein the second primer corresponds to a region of a second chromosome.

9. The method of claim 1, wherein the DNA sample is obtained from chorionic villus, placental biopsies, amniotic fluid, fetal blood, fetal serum, fetal plasma, maternal blood, maternal serum, or maternal plasma.

* * * * *

UNITED STATES PATENT AND TRADEMARK OFFICE
CERTIFICATE OF CORRECTION

| | | |
|---|---|---|
| PATENT NO. | : 7,981,607 B2 | Page 1 of 1 |
| APPLICATION NO. | : 11/661528 | |
| DATED | : July 19, 2011 | |
| INVENTOR(S) | : Anthony P. Shuber | |

It is certified that error appears in the above-identified patent and that said Letters Patent is hereby corrected as shown below:

Page 1, Column 1, Field 54, After "DETECTING", insert -- A --.

Page 2, Column 2, Line 47, insert -- EP 0259031 B1   11/1994 --.

Column 13, Line 58, delete "(p23;q3 5);", insert -- (p23:q35) --.

Column 14, Line 3, delete "t(6;1)", insert -- t(6;11) --.

Column 14, Line 9, delete "t(7;1)", insert -- t(7;11) --.

Column 14, Line 9, delete "t(7;11 )", insert -- t(7;11) --.

Column 14, Line 42, delete "(p1.2;q23)", insert -- (p11.2;q23) --.

Column 14, Line 58, delete "t(7:1)", insert -- t(7:11) --.

Column 15, Line 67, delete "t(1;", insert -- t(11; --.

Column 16, Line 3, delete "(p1;q21)", insert -- (p11;q21) --.

Column 16, Line 7, delete "t(1;", insert -- t(11; --.

Column 16, Line 36, delete "(q2;q11)", insert -- (q21;q11) --.

Column 16, Line 36, delete "(q2;q11)", insert -- (q21;q11) --.

Signed and Sealed this
Twenty-second Day of November, 2011

David J. Kappos
*Director of the United States Patent and Trademark Office*